US011759620B2

(12) United States Patent
Potenziano et al.

(10) Patent No.: US 11,759,620 B2
(45) Date of Patent: Sep. 19, 2023

(54) USE AND MONITORING OF INHALED NITRIC OXIDE WITH LEFT VENTRICULAR ASSIST DEVICES

(71) Applicant: Mallinckrodt Pharmaceuticals Ireland Limited, Dublin (IE)

(72) Inventors: Jim Potenziano, Binghamton, NY (US); Douglas Alan Greene, Basking Ridge, NJ (US); Craig Flanagan, Belmar, NJ (US)

(73) Assignee: MALLINCKRODT PHARMACEUTICALS IRELAND LIMITED, Dublin (IE)

(*) Notice: Subject to any disclaimer, the term of this patent is extended or adjusted under 35 U.S.C. 154(b) by 117 days.

(21) Appl. No.: 17/358,738

(22) Filed: Jun. 25, 2021

(65) Prior Publication Data

US 2021/0330957 A1    Oct. 28, 2021

Related U.S. Application Data

(62) Division of application No. 16/077,276, filed as application No. PCT/US2017/015552 on Jan. 30, 2017, now Pat. No. 11,202,899.

(Continued)

(51) Int. Cl.
*A61M 60/148* (2021.01)
*A61M 60/538* (2021.01)
(Continued)

(52) U.S. Cl.
CPC ....... *A61M 60/148* (2021.01); *A61B 5/02007* (2013.01); *A61B 5/029* (2013.01);
(Continued)

(58) Field of Classification Search
CPC .. A61M 60/148; A61M 60/178; A61M 60/20; A61M 60/515; A61M 60/538;
(Continued)

(56) References Cited

U.S. PATENT DOCUMENTS

| 5,396,882 A | 3/1995 | Zapol |
| 5,558,083 A | 9/1996 | Bathe et al. |

(Continued)

FOREIGN PATENT DOCUMENTS

| JP | 2014506872 A | 3/2014 |
| WO | 2006122005 A2 | 11/2006 |

(Continued)

OTHER PUBLICATIONS

Argenziano M., et al., "Randomized, Double-Blind Trial of Inhaled Nitric Oxide in LVAD Recipients with Pulmonary Hypertension," The Annals of Thoracic Surgery, 1998, vol. 65, No. 2, pp. 340-345.

(Continued)

*Primary Examiner* — Amanda K Hulbert
*Assistant Examiner* — Natasha Patel

(57) ABSTRACT

Described are systems and methods for administration of nitric oxide (NO) with use of left ventricular assists devices (LVADs), as well as systems and methods for monitoring the NO delivery devices and/or the LVAD.

5 Claims, 18 Drawing Sheets

Related U.S. Application Data

(60) Provisional application No. 62/294,711, filed on Feb. 12, 2016.

(51) Int. Cl.

| | | |
|---|---|---|
| *A61M 60/515* | (2021.01) | |
| *A61M 60/178* | (2021.01) | |
| *A61M 60/20* | (2021.01) | |
| *A61B 5/02* | (2006.01) | |
| *A61B 5/0215* | (2006.01) | |
| *A61B 5/029* | (2006.01) | |
| *A61B 5/00* | (2006.01) | |
| *A61B 8/08* | (2006.01) | |
| *A61B 5/08* | (2006.01) | |
| *G16H 50/30* | (2018.01) | |
| *G16H 20/40* | (2018.01) | |

(52) U.S. Cl.
CPC .......... *A61B 5/0215* (2013.01); *A61B 5/4842* (2013.01); *A61B 5/4848* (2013.01); *A61B 5/686* (2013.01); *A61B 5/7275* (2013.01); *A61B 8/0883* (2013.01); *A61M 60/178* (2021.01); *A61M 60/20* (2021.01); *A61M 60/515* (2021.01); *A61M 60/538* (2021.01); *A61B 5/0816* (2013.01); *A61M 2202/0275* (2013.01); *A61M 2205/05* (2013.01); *A61M 2205/3303* (2013.01); *A61M 2205/3553* (2013.01); *A61M 2230/04* (2013.01); *G16H 20/40* (2018.01); *G16H 50/30* (2018.01)

(58) Field of Classification Search
CPC ...... A61M 2202/0275; A61M 2205/05; A61M 2205/3303; A61M 2205/3553; A61M 2230/04; A61B 5/02007; A61B 5/0215; A61B 5/029; A61B 5/4842; A61B 5/4848; A61B 5/686; A61B 5/7275; A61B 8/0883; A61B 5/0816; G16H 20/40; G16H 50/30; A61P 9/04; A61P 9/12; A61P 11/00
See application file for complete search history.

(56) References Cited

U.S. PATENT DOCUMENTS

| | | | |
|---|---|---|---|
| 7,523,752 | B2 | 4/2009 | Montgomery et al. |
| 7,560,076 | B2 | 7/2009 | Rounbehler et al. |
| 8,573,209 | B2 | 11/2013 | Bathe et al. |
| 8,573,210 | B2 | 11/2013 | Bathe et al. |
| 8,770,199 | B2 | 7/2014 | Flanagan et al. |
| 2007/0021358 | A1* | 1/2007 | Edelman ............ A61K 31/4166 514/649 |
| 2008/0031818 | A1 | 2/2008 | Bush et al. |
| 2008/0228456 | A1 | 9/2008 | Clermont et al. |
| 2010/0331405 | A1* | 12/2010 | Baldassarre ....... A61B 5/02007 514/509 |
| 2012/0093948 | A1* | 4/2012 | Fine ........................ A61P 25/34 424/718 |
| 2013/0309328 | A1* | 11/2013 | Watts ..................... A61P 11/00 128/203.12 |
| 2014/0163397 | A1 | 6/2014 | Anderson et al. |
| 2014/0283828 | A1 | 9/2014 | Acker et al. |

FOREIGN PATENT DOCUMENTS

| | | |
|---|---|---|
| WO | 2012075420 A1 | 6/2012 |
| WO | 2015084698 A2 | 6/2015 |

OTHER PUBLICATIONS

Chang J-C., et al., "Hemodynamic Effect of Inhaled Nitric Oxide in Dilated Cardiomyopathy patients on LVAD Support", ASAIO Journal, 1997, vol. 43 (5), pp. M418-M421.

Endo G.J., et al., "Nitric Oxide Inhalation Prompts Weaning From the Right Ventricular Assist Device: Evaluation Under Continuous-Flow Biventricular Assistance," The Journal of Thoracic and Cardiovascular Surgery, Feb. 10, 2002, vol. 124, No. 4, doi: 10.1067/mtc.2002.124669, pp. 739-749.

English Translated Office Action for Japanese Patent Application No. 2018-542275, dated Nov. 13, 2020, 6 pages.

English Translated Second Office Action for Chinese Application No. 201780018861.4, dated Nov. 17, 2020, 11 pages.

Estep J.D., et al., "The Role of Echocardiography and Other Imaging Modalities in Patients With Left Ventricular Assist Devices," JACC: Cardiovascular Imaging, vol. 03, No. 10, Jul. 20, 2010, doi: 10.1016/j.jcmg.2010.07.012, pp. 1049-1064.

Examination Report No. 1 for Australian Patent Application No. 2017218391 dated Jan. 20, 2022, 3 pages.

Examination Report No. 2 for Australian Patent Application No. 2017218391 dated May 31, 2022, 3 Pages.

Examination Report No. 3 for Australian Patent Application No. 2017218391 dated Aug. 29, 2022, 3 pages.

Extended European Search Report for Application No. 21206569.2, dated Feb. 23, 2022, 9 Pages.

Extended European Search Report for European Application No. 17750567.4, dated Sep. 3, 2019, 14 Pages.

Ichinose F., et al., "Inhaled Nitric Oxide, A Selective Pulmonary Vasodilator Current Uses and Therapeutic Potential," Circulation, Jun. 29, 2004, vol. 109, pp. 3106-3111.

International Preliminary Report on Patentability for International Application No. PCT/US2017/015552, dated Aug. 23, 2018, 8 pages.

International Search Report and Written Opinion for International Application No. PCT/US2017/015552, dated Jun. 5, 2017, 12 pages.

International Search Report for International Application No. PCT/US2017/015552, dated Jun. 5, 2017, 5 pages.

Kutty R.S., et al., "Use of Centrifugal Left Ventricular Assist Device as a Bridge to Candidacy in Severe Heart Failure with Secondary Pulmonary Hypertension," European Journal of Cardio-Thoracic Surgery, 2013, vol. 43 (6), pp. 1237-1242.

Lovich M.A., et al., "Inhaled Nitric Oxide Augments Left Ventricular Assist Device Capacity by Ameliorating Secondary right Ventricular Failure," ASAIO Journal, 2015, vol. 61 (4), pp. 379-385.

Office Action for European Patent Application No. 17750567.4, dated Jun. 30, 2021, 9 pages.

Office Action for Japanese Application No. 2021-163373, dated Sep. 29, 2022, 9 pages.

Office Action for Japanese Patent Application No. 2021163373, dated Jun. 17, 2022, 7 pages.

Partial Supplementary European Search Report for European Application No. 17750567.4, dated Jul. 4, 2019, 11 Pages.

Search Report for Chinese Patent Application No. 201780018861.4, dated Nov. 11, 2020, 3 pages.

\* cited by examiner

USE AND MONITORING OF INHALED NITRIC OXIDE WITH LEFT VENTRICULAR ASSIST DEVICES

CROSS-REFERENCE TO RELATED APPLICATIONS

This application is a divisional of U.S. application Ser. No. 16/077,276, filed Aug. 10, 2018 which claims priority to U.S. Application No. 62/294,711, filed on Feb. 12, 2016 the, each of which is hereby incorporated by reference in its entirety.

TECHNICAL FIELD

Embodiments of the present invention generally relate to the field of methods and devices for delivering and monitoring inhaled nitric oxide (NO).

BACKGROUND

Modern semi-permanent continuous-flow left ventricular assist devices (LVADs) are cost-effective and durable surgically-implanted mechanical devices which augment or substitute for a poorly functioning or nonfunctioning diseased left ventricle of the heart to maintain blood circulation to the body. LVADs are now considered to be a reasonable alternative to orthotopic heart transplantation, especially given the severe shortage of suitable donor organs. Continuous-flow LVADs have replaced earlier pulsatile models because they are more durable, less cumbersome, and have been shown to increase survival, exercise capacity and quality of life. LVADs are used to sustain patients with advanced congestive heart failure (CHF) who cannot be managed medically either as a bridge-to-heart transplantation, as destination therapy or, in those patients whose CHF is deemed at least partially reversible, as a bridge-to-recovery. The frequency of sufficient recovery to permit LVAD explantation is estimated to be 10-20% in CHF of non-ischemic etiology and in <1% in ischemic CHF. LVAD implantation is generally indicated in CHF when cardiac index (CI) is <2 L/min/m$^2$, systemic systolic arterial pressure is <90 mm Hg, left atrial pressure is >20 mm Hg, or the systemic vascular resistance is >1.57 mm Hg/mL. Advances in the durability and miniaturization of LVADs, afforded by continuous-flow rather than pulsatile design, have enabled more extensive and longer-duration utilization.

Unfortunately, failure of the right ventricle has been reported in 15% of continuous-flow LVAD recipients within the first 30 days following implantation and in 20-50% of LVAD recipients overall. As such, right ventricular failure remains a major limitation of LVAD utility, and is associated with markedly poorer prognosis.

Furthermore, continuous-flow LVADs generate reduced pulsatility of peripheral perfusion compared to pulsatile-flow LVAD devices and/or the normal circulation derived from a well-functioning human heart as measured by pulsatility index, pulse pressure and/or the frequency of opening of the aortic valve, and this reduced pulsatility has been implicated in a number of adverse events including reduced peripheral vascular compliance, gastrointestinal bleeding, arteriovenous malformations, hemolysis, pump thrombosis, aortic insufficiency and lower rate of recovery of left ventricular function.

Accordingly, there is a need for adjunctive therapies that enhance the use of LVADs and/or reduce the risk of right ventricular failure associated with LVADs and/or reduce the risk of other LVAD-related adverse events.

SUMMARY

One or more aspects of the present invention provide new adjunctive therapies that enhance the effectiveness of LVADs and/or reduce the risk of right ventricular failure associated with LVADs.

One aspect of the present invention relates to a method of determining whether a patient with pulmonary hypertension will resolve the pulmonary hypertension with continued use of an LVAD. In various embodiments of this aspect, the method comprises measuring one or more pulmonary hemodynamic parameters of a patient with an LVAD to obtain a first pulmonary hemodynamic value; after obtaining the first pulmonary hemodynamic value, administering inhaled NO to the patient with the LVAD; and measuring one or more pulmonary hemodynamic parameters of the patient during or after the inhaled NO administration to obtain a second pulmonary hemodynamic value. A significant change in the pulmonary hemodynamic parameter from the first pulmonary hemodynamic value to the second pulmonary hemodynamic value can indicate that the patient is likely to resolve the pulmonary hypertension after continued use of the LVAD. For example, a significant change in the pulmonary hemodynamic parameter can be at least 10 mm Hg mPAP and/or at least 20% PVR, or equivalent changes as shown by echocardiography, MRI or other imaging technology.

In some embodiments of this aspect, the inhaled NO is administered at a concentration of 5 to 80 ppm for at least 10 minutes. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 10 minutes, about 15 minutes, about 20 minutes, about 25 minutes, about 30 minutes, about 35 minutes, about 40 minutes, about 45 minutes, about 50 minutes, about 55 minutes, and about 60 minutes.

Exemplary pulmonary hemodynamic parameters include mean pulmonary artery pressure (mPAP), diastolic pulmonary artery pressure (dPAP), pulmonary capillary wedge pressure (PCWP), transpulmonary gradient (TPG) and pulmonary vascular resistance (PVR). Other pulmonary hemodynamic parameters include combinations of and/or inter-relations between these parameters, such as the difference between dPAP and PCWP. The one or more pulmonary hemodynamic parameters may be measured or estimated by any appropriate procedures, such as by performing a right heart catheterization, MRI or echocardiography.

In one or more embodiments, the method further comprises placing the patient on a heart transplant list if there is a significant change in the pulmonary hemodynamic parameter from the first pulmonary hemodynamic value to the second pulmonary hemodynamic value, such as a decrease in mPAP of at least 10 mm Hg and/or a decrease in PVR at least 20%. In some embodiments, the method further comprises explanting the LVAD and implanting a donor heart in the patient.

As an alternate to the above thresholds of 10 mm Hg mPAP and/or 20% PVR, other significant changes in the pulmonary hemodynamic parameter may be a decrease of 5 mm Hg (for pressure-related parameters such as mPAP or TPG) or a change in the parameter of at least 5% (for all parameters). Exemplary significant changes in the pulmonary hemodynamic parameter include a change of at least 5 mm Hg, at least 6 mm Hg, at least 7 mm Hg, at least 8 mm Hg, at least 9 mm Hg, at least 10 mm Hg, at least 15 mm Hg, at least 20 mm Hg, or at least 25 mm Hg, and/or at least 5%, at least 10%, at least 15%, at least 20%, at least 25%, at least 30%, at least 35%, at least 40% or at least 50%.

Another aspect of the present invention relates to a method of optimizing the settings of an LVAD. In various embodiments of this aspect, the method comprises administering inhaled NO to a patient having an LVAD; performing an echocardiogram on the patient during the administration of inhaled NO; and adjusting or setting one or more parameters of the LVAD during the echocardiogram and during the administration of inhaled NO. Instead of performing an echocardiogram, other appropriate techniques may be used to set the LVAD parameters. In one or more embodiments, adjusting or setting the LVAD parameters during administration of NO helps to optimize cardiac output.

In one or more embodiments of this aspect, adjusting or setting one or more parameters of the LVAD comprises one or more of (i) determining a low pump speed setting for the LVAD based on the minimal pump speed necessary for the patient's aortic valve to open with each heart beat or (ii) determining a high speed setting for the LVAD based on the pump speed at which the septum of the patient's heart flattens. In some embodiments, augmenting aortic valve opening and closing without flattening the septum could include setting a constant speed, or setting a range over which the speed could be modulated to accomplish this, such as in pulse modulation continuous flow.

In some embodiments of this aspect, the inhaled NO is administered at a concentration of 5 to 80 ppm for at least 10 minutes. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1.5 hours, about 2 hours, about 2.5 hours and about 3 hours.

In some embodiments, the LVAD settings are changed over a series of incremental adjustments. For example, the LVAD pump speed may be adjusted upwards in two or more steps. One or more or all of these steps may be performed during the administration of inhaled NO as described herein.

Another aspect of the present invention relates to a method of reducing the risk of right ventricular failure during LVAD use. In various embodiments of this aspect, the method comprises administering inhaled NO to a patient with an LVAD for at least 12 hours a day for at least 20 days.

Due to the fact that a patient with an LVAD had preexisting left ventricular dysfunction, it may be important to ensure that the LVAD is properly functioning prior to administering inhaled NO. Accordingly, in some embodiments, the method further comprises confirming that the LVAD is functioning properly before administering inhaled NO.

In one or more embodiments, the inhaled NO is administered after a patient has been weaned from cardiopulmonary bypass (CPB).

The inhaled NO may be administered for several days to many months or even longer. Exemplary treatment times include 10 days, 15 days, 20 days, 25 days, 30 days, 35 days, 40 days, 45 days, 2 months, 3 months, 4 months, 5 months, 6 months, 7 months, 8 months, 9 months, 10 months, 11 months, 1 year, 1.5 years, or 2 years. In some embodiments, the patient is administered inhaled NO indefinitely.

In some embodiments of this aspect, the inhaled NO is administered at a concentration of 5 to 80 ppm for at least 12 hours a day. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 12 hours a day, about 14 hours a day, about 16 hours a day, about 18 hours a day, about 20 hours a day, about 22 hours a day, or up to 24 hours a day.

Alternatively, the dose of NO may be prescribed based on the patient's ideal body weight (IBW). Exemplary NO doses may be in the range of about 25 to about 150 µg/kg IBW/hr, such as about 25, about 30, about 35, about 40, about 45, about 50, about 60, about 70, about 80, about 90, about 100, about 110, about 120, about 130, about 140 or about 150 µg/kg IBW/hr.

In one or more embodiments, the method further comprises monitoring one or more output parameters of the LVAD and/or one or more hemodynamic parameters of the patient, comparing the one or more output parameters and/or the one or more hemodynamic parameters to a predetermined range, and adjusting the dose of inhaled NO if the one or more outputs parameters and/or the one or more hemodynamic parameters are outside of the predetermined range. In some embodiments, the method further comprises providing an alert if the one or more output parameters and/or the one or more hemodynamic parameters are outside of the predetermined range. Such alerts can include an audible alert, a visual alert, a somatosensory alert (e.g. vibration) and/or a text alert. The inhaled NO dose may be adjusted automatically (e.g. by the NO delivery device or a control system in communication with the NO delivery device), or may be manually adjusted by a physician or other user.

Examples of LVAD parameters that may be monitored include, but are not limited to, pump speed (e.g. rpm), pump flow (e.g. L/min), pulsatility index, battery level, and LVAD status (e.g. operational, presence or absence of warnings).

Another aspect of the present invention relates to a method of monitoring the left ventricle of a patient with an LVAD to determine whether the left ventricle of the patient is improving. In various embodiments of this aspect, the method comprises reducing the pump speed of the LVAD or turning off the LVAD; measuring one or more pulmonary hemodynamic parameters of the patient to obtain a first pulmonary hemodynamic value; preloading the left ventricle by administering inhaled NO to the patient; and measuring one or more pulmonary hemodynamic parameters after or during administration of inhaled NO to obtain a second pulmonary hemodynamic value. In some embodiments, the pulmonary hemodynamic parameter is selected from LAP, PCWP and CO, or may be any assessment of the left ventricular reserve to compensate for increased left ventricular preload that can be measured through right heart catheterization, echocardio graphic, MRI or other techniques.

In some embodiments of this aspect, the inhaled NO is administered at a concentration of 5 to 80 ppm for at least 10 minutes. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1.5 hours, about 2 hours, about 2.5 hours, about 3 hours, about 3.5 hours, about 4 hours, about 5 hours, about 6 hours, about 7 hours or about 8 hours.

According to one or more embodiments, an increase in LAP and/or PCWP from the first pulmonary hemodynamic value to the second pulmonary hemodynamic value of less than 5 mm Hg indicates that the left ventricle is improving. Other exemplary values that indicate an improvement in the left ventricle include an LAP and/or PCWP increase of less than 1 mm Hg, 2 mm Hg, 3 mm Hg, 4 mm Hg, 6 mm Hg, 7 mm Hg, 8mm Hg, 9 mm Hg, 10 mm Hg, 11 mm Hg, 12 mm Hg, 13 mm Hg, 14 mm Hg or 15 mm Hg. In some embodiments, the method further comprises modifying treatment if the left ventricle is improving, such as explanting the LVAD from the patient. Other modifications in treatment can include changing the supportive medication (e.g. diuretics and/or inotropic medications) that the patient is given, such as reducing the supportive medication.

Yet another aspect of the present invention relates to a method of exercising a heart of a patient having an LVAD. In various embodiments of this aspect, the method comprises reducing and/or modulating the pump speed of the LVAD or turning off the LVAD; preloading the left ventricle by administering inhaled NO to the patient for at least 5 minutes; discontinuing the inhaled NO administration; and repeating the preloading and discontinuation to exercise the left ventricle of the patient's heart.

In some embodiments of this aspect, the inhaled NO is administered at a concentration of 5 to 80 ppm for at least 5 minutes. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1.5 hours, about 2 hours, about 2.5 hours, about 3 hours, about 3.5 hours, about 4 hours, about 5 hours, about 6 hours, about 7 hours or about 8 hours.

Alternatively, the dose of NO may be prescribed based on the patient's ideal body weight (IBW). Exemplary NO doses may be in the range of about 25 to about 150 μg/kg IBW/hr, such as about 25, about 30, about 35, about 40, about 45, about 50, about 60, about 70, about 80, about 90, about 100, about 110, about 120, about 130, about 140 or about 150 μg/kg IBW/hr.

The preloading of the left ventricle may be performed multiple times per day, such as twice a day, three times a day, four times a day, five times a day, six times a day, seven times a day, eight times a day, nine times a day or ten times a day. Alternatively, the preloading may be performed once a day. If the preloading is performed multiple times per day, the preloading procedures may be clustered together (e.g. spaced apart by several minutes or a couple hours) or may be spread out throughout the day. The preloading of the left ventricle may also be performed once a week, two days a week, three days a week, four days a week, five days a week, six days a week, or seven days a week. In exemplary embodiments, the left ventricle is preloaded several times a day for several days a week, such as two to five times a day for two to four days a week or other combinations of the above daily and weekly preloading schedules.

Yet another aspect of the present invention relates to a method of reducing the risk of adverse events during LVAD use. In various embodiments of this aspect, the adverse events are associated with reduced pulsatility caused by LVAD use and/or associated with impaired NO-mediated vascular function.

In various embodiments of this aspect, the method comprises administering inhaled NO to a patient with a continuous-flow or semi-pulsatile LVAD for at least 12 hours a day for at least 20 days.

Due to the fact that a patient with an LVAD had preexisting left ventricular dysfunction, it may be important to ensure that the LVAD is properly functioning prior to administering inhaled NO. Accordingly, in some embodiments, the method further comprises confirming that the LVAD is functioning properly before administering inhaled NO.

In one or more embodiments, the inhaled NO is administered after a patient has been weaned from cardiopulmonary bypass (CPB).

The inhaled NO may be administered for several days to many months or even longer. Exemplary treatment times include 10 days, 15 days, 20 days, 25 days, 30 days, 35 days, 40 days, 45 days, 2 months, 3 months, 4 months, 5 months, 6 months, 7 months, 8 months, 9 months, 10 months, 11 months, 1 year, 1.5 years, or 2 years. In some embodiments, the patient is administered inhaled NO indefinitely.

In some embodiments of this aspect, the inhaled NO is administered at a concentration of 5 to 80 ppm for at least 12 hours a day. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 12 hours a day, about 14 hours a day, about 16 hours a day, about 18 hours a day, about 20 hours a day, about 22 hours a day, or up to 24 hours a day.

Alternatively, the dose of NO may be prescribed based on the patient's ideal body weight (IBW). Exemplary NO doses may be in the range of about 25 to about 150 fig/kg IBW/hr, such as about 25, about 30, about 35, about 40, about 45, about 50, about 60, about 70, about 80, about 90, about 100, about 110, about 120, about 130, about 140 or about 150 μg/kg IBW/hr.

In one or more embodiments, the method further comprises monitoring one or more output parameters of the LVAD and/or one or more hemodynamic parameters of the patient, comparing the one or more output parameters and/or the one or more hemodynamic parameters to a predetermined range, and adjusting the dose of inhaled NO if the one or more outputs parameters and/or the one or more hemodynamic parameters are outside of the predetermined range. In some embodiments, the method further comprises providing an alert if the one or more output parameters and/or the one or more hemodynamic parameters are outside of the predetermined range. Such alerts can include an audible alert, a visual alert, a somatosensory alert (e.g. vibration) and/or a text alert. The inhaled NO dose may be adjusted automatically (e.g. by the NO delivery device or a control system in communication with the NO delivery device), or may be manually adjusted by a physician or other user.

Examples of LVAD parameters that may be monitored include, but are not limited to, pump speed (e.g. rpm), pump flow (e.g. L/min), pulsatility index, battery level, and LVAD status (e.g. operational, presence or absence of warnings).

Yet another aspect relates to a method of optimizing the inhaled NO dose to be used in conjunction with an LVAD, such as a continuous-flow or semi-pulsatile LVAD. In various embodiments of this aspect, the method comprises measuring endothelial function of a patient having a continuous-flow or semi-pulsatile LVAD, administering inhaled NO to the patient at a first dose, measuring the endothelial function of the patient during the administration of inhaled NO, and adjusting the inhaled NO dose to optimize endothelial function. Any appropriate techniques may be used to measure the endothelial function, including, but not limited to, flow-mediated dilation (FMD) and/or reactive hyperemic index (RHI). In one or more embodiments, adjusting the NO dose helps to optimize the endothelial function and reduce the risk of adverse events associated with impaired NO-mediated vascular function.

In some embodiments, the method further comprises measuring one or NO-related molecules and/or other biomarkers of endothelial function in the patient's blood and/or plasma. Exemplary NO-related molecules include whole blood and erythrocyte nitrite ($NO2^-$), nitrate ($NO3^-$) heme-nitrosylated hemoglobin [Hb(FeII)NO] and cysteine nitrosylated hemoglobin (also known as S-nitrosohemoglobin SNO-Hb), and nitrosylated plasma proteins. Other biomarkers of endothelial function include, but are not limited to, pulse amplitude tonometry (measuring post ischemic swelling of the fingertip) and peripheral arterial tonometry (using ultrasound to measure the size of the brachial artery after a blood pressure cuff is released)..

Yet another aspect of the present invention relates to a system for coordinating operation of the LVAD and the NO delivery device. Such a system may be used in any of the indications or methods described herein. In various embodiments of this aspect, the system comprises a control system in communication with the NO delivery device and/or the LVAD, wherein the control system monitors one or more parameters of the NO delivery device and/or one or more parameters of the LVAD and provides an alert if one or more parameters of the NO delivery device and/or LVAD are outside of a predetermined range. The system may also comprise the NO delivery device and/or the LVAD itself.

In one or more embodiments, the control system reduces a pump speed of the LVAD if there is a failure of the NO delivery device. The control system may also initiate a weaning procedure for the NO delivery device if there is a failure of the LVAD.

The control system may be integral to the NO delivery device, integral to the LVAD or a component of a stand-alone control module.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Nitric Oxide for Inhalation

Figure 1:
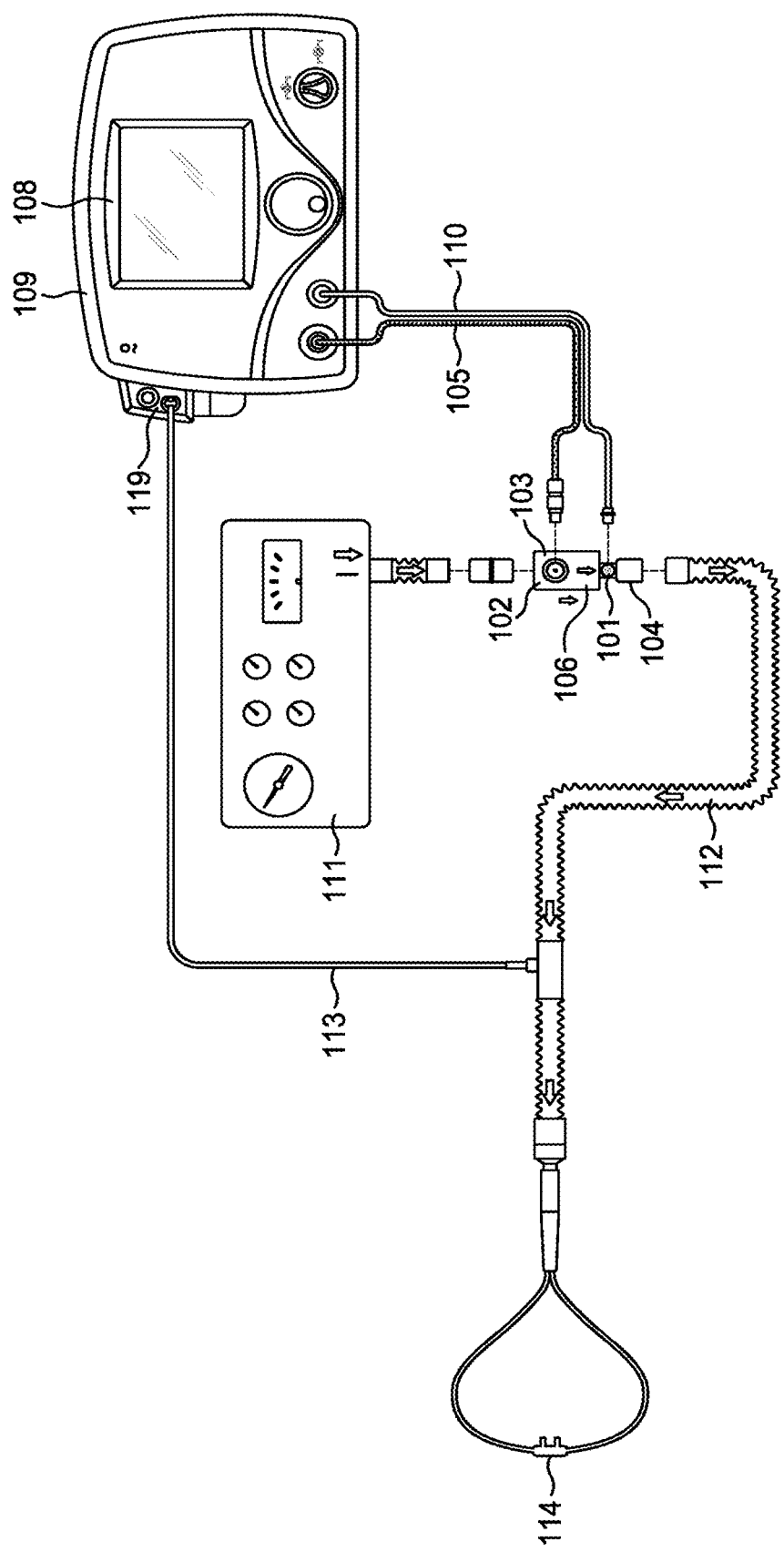
FIG. 1 illustrates an exemplary NO delivery device that can be used in accordance with one or more embodiments of the invention

INOmax® (nitric oxide) for inhalation is an approved drug product. The FDA-approved prescribing information for INOmax® dated 2013 is attached as Appendix 1, and so fauns part of the present disclosure, and also is incorporated by reference herein in its entirety. INOmax® is a selective pulmonary vasodilator, which, in conjunction with ventilatory support or other appropriate agents, is indicated for the treatment of term and near-term (>34 weeks gestation) neonates with hypoxic respiratory failure associated with clinical or echocardiographic evidence of pulmonary hypertension, where it improves oxygenation and reduces the need for extracorporeal membrane oxygenation. The recommended dose of INOmax® for the approved indication is 20 ppm, maintained for up to 14 days or until the underlying oxygen desaturation has resolved. Weaning should occur gradually. Adverse reactions per the label include methemoglobinemia and nitrogen di oxide levels, both which can be dose dependent.

Inhaled NO may be administered via a NO delivery device such as the INOmax DSIR®, INOmax® DS or INOvent® delivery devices, each of which delivers operator-determined concentrations of NO in conjunction with a ventilator or breathing gas administration system after dilution with oxygen or an oxygen/air mixture. Other NO delivery devices and features of NO delivery devices are described below, including NO delivery devices having novel features not present in currently available NO delivery devices.

The source of NO used in any of the presently disclosed methods and devices can be a cylinder of compressed gas containing NO, typically as a mixture with an inert gas such as nitrogen or helium. The NO-containing gas can be generated by manufacturing the gases separately, mixing them in an appropriate ratio, and introducing them into an appropriate cylinder under pressure. The mixing can occur in two steps: first diluting bulk NO with nitrogen to a concentration of, e.g., 5,000 ppm or 28,600 ppm in interim cylinders, and then diluting that mixture further by introducing the mixture into the final cylinders and filling them with more nitrogen to produce a concentration of, e.g., 100 ppm or 800 ppm in the final cylinders. Care is taken not to introduce any water or oxygen into the cylinders. The cylinders can be equipped with an appropriate valve, shipped to the point of use, and attached to a NO delivery device to facilitate inhalation of the gas by the patient.

The source of NO can instead be a NO-generating device that generates NO from a suitable nitrogen source, such as air (see for reference U.S. Pat. No. 5,396,882, incorporated herein by reference) or nitrogen dioxide (see for reference U.S. Pat. No. 7,560,076, incorporated herein by reference). The source of nitrogen dioxide can be, for example, a canister of compressed nitrogen dioxide gas or a container of N204 (which, when treated under appropriate conditions, will give off nitrogen dioxide). Manufacturing a source of nitrogen dioxide can include the steps of compressing nitrogen dioxide gas into a suitable container or introducing N204 in liquid form into a suitable container. The container can be supplied in a device that includes a filter containing a reducing agent or antioxidant, such as ascorbic acid, which reduces the nitrogen dioxide to form NO at the patient's bedside. At the point of administration, such a NO-generating device is typically attached to a gas-delivery device (such as a ventilator) to facilitate inhalation of the newly foamed NO gas by the patient.

Definitions

As used herein, the tetra "pulmonary hemodynamic parameter" refers to any parameter used to describe or evaluate the blood flow through the heart and pulmonary vasculature. Examples of pulmonary hemodynamic parameters include, but are not limited to, mean pulmonary artery pressure (mPAP), diastolic pulmonary artery pressure (dPAP) [also known as pulmonary artery diastolic pressure (PADP)], systolic pulmonary artery pressure (sPAP) [also known as pulmonary artery systolic pressure (PASP)], pulmonary capillary wedge pressure (PCWP) [also known as pulmonary artery wedge pressure (PAWP)], left atrial pressure (LAP), transpulmonary gradient (TPG), pulmonary vascular resistance (PVR) and cardiac output (CO).

Many of the pulmonary hemodynamic parameters described above are interrelated. For example, PCWP is often used as a more convenient, less invasive approximation of LAP. As another example, PVR is related to mPAP, PCWP and CO according to the following equation:

$$PVR \, \alpha \, (mPAP-PCWP)/CO$$

As yet another example, TPG is the difference between mPAP and PCWP as shown by the following equation:

$$TPG=mPAP-PCWP$$

As a further example, mPAP is related to dPAP and sPAP according to the following equation:

$$mPAP=(2/3)dPAP+(1/3)sPAP$$

In some embodiments, the pulmonary hemodynamic parameters are measured directly, such as during a right heart catheterization. In other embodiments, the pulmonary hemodynamic parameters are estimated and/or evaluated through other techniques such as magnetic resonance imaging (MRI) or echocardiography.

The phrase "resolution of pulmonary hypertension (PH)" or variations thereof refers to a decrease in PH below a clinically relevant threshold. One example of resolution of PH is when the mPAP of a patient decreases below a threshold of 25 mmHg. However, in patients with severe right ventricular failure, the ventricle can be so weak that it cannot generate sufficient force to raise sPAP so that the mPAP is at least 25 mmHg. In such patients, PH and resolution thereof may be evaluated by analyzing the difference between dPAP and PCWP.

Right Ventricular Failure in LVAD Implanted Patients

As described above, right ventricular failure is a common problem after LVAD implantation. Post-LVAD right-sided heart failure is primarily related to the dynamic effects of the LVAD itself and/or the underlying right ventricular disease, as post-operative right heart failure occurs in only a small proportion of orthotopic heart transplants when performed in a similar population.

Post-LVAD right ventricular failure may be defined pathophysiologically as inability of the right ventricle to maintain adequate loading of the LVAD-assisted left ventricle despite adequate right ventricle preload, or to do so only at the expense of significantly elevated central venous pressure. Post-LVAD right heart failure is generally defined operationally as the need for implantation of a right ventricular assist device (RVAD), or the need for reinstitution of inhaled NO for greater than 48 hours, or the need for inotropic pharmacological therapy for greater than 14 days. Recent retrospective studies have each implicated various different pre-implantation clinical and hemodynamic parameters as being predictive of post-LVAD right heart failure with little consensus as to the most informative or most predictive factors; thus full understanding and accurate prediction of post-implantation right heart failure remains clinically problematic and mechanistically controversial. Putative predictive factors have ranged from non-specific demographic, clinical and laboratory measures of overall disease burden or patient "frailty", to conventional hemodynamic and echocardiographic measures of left ventricle, right ventricle and pulmonary vascular status, to very specific and specialized functional imaging parameters of the right ventricle. The pathophysiology of right ventricular failure after LVAD implantation appears to be multi-factorial, and includes pre-operative right ventricular dysfunction and pulmonary hypertension (PH), right ventricular ischemia, peri-operative fluctuations in pulmonary vascular resistance (PVR) in the setting of cardiopulmonary bypass (CPB), excessive right ventricular preload, and altered interventricular balance, although the relative importance of each of these factors is strongly debated. Superimposed perioperative procedures and/or complications thereof, such as intra-operative mechanical and/or ischemic damage to the right ventricle, and intra-operative hemorrhage requiring extensive fluid, colloid or blood product resuscitation, have also been invoked as acute predisposing or exacerbating factors for peri-operative right heart failure associated with LVAD implantation. Importantly, the direct and indirect effects of the LVAD itself on the anatomy and function of the left ventricle are also implicated as causing or contributing to post-implantation right ventricular dysfunction and right heart failure, despite optimization of LVAD adjustments and pharmacological support.

Interactions Between the Left and Right Ventricles in Congestive Heart Failure

In the healthy heart, the left ventricle is estimated to contribute 80% of the contractile flow and up to two-thirds of the contractile pressure generated by the right ventricle through a process tamed mechanical systolic ventricular interaction (SVI). The (patho)physiological interactions between the left ventricle and the right ventricle in CHF are quite complex. The right ventricle may be directly damaged by the underlying disease process affecting the left ventricle in CHF. Most commonly, right ventricular failure in CHF results from increased right ventricular afterload due to chronic pulmonary vascular congestion and PH consequent to the primary left ventricular dysfunction. Additionally, dilation of the left ventricle in CHF realigns the anatomy of interventricular septal musculature to a less efficient transverse orientation, further impairing SVI and therefore overall right ventricular contractility. When combined with the increased right ventricle afterload, dysfunctional SVI unleashes a vicious cycle of progressive right ventricular dysfunction and right ventricular failure Reciprocally, as the failing right ventricle dilates, it intrudes and interferes with the relaxation (diastolic) filling of the left ventricle (termed diastolic ventricular interaction [DVI]), further exacerbating pulmonary vascular congestion and PH, creating a superimposed additional vicious cycle of progressive left ventricular failure and right ventricular failure. An additional form of remote interventricular interaction occurs at the level of the peripheral circulation, wherein the increased central systemic blood volume and central venous pressure in CHF increases right ventricular preload and right ventricular filling further increasing interventricular septal intrusion into the left ventricle and thereby further worsening DVI. Lastly, a further level of interventricular interaction occurs at the level of the pulmonary circulation, where chronic elevation of pulmonary venous and capillary pressures causes pulmonary vascular remodeling which, over time creates a relatively fixed, structurally-mediated increase in PVR, further worsening PH and right ventricular afterload (defined as World Health Organization [WHO] Group 2 Pulmonary Hypertension Secondary to Left-Sided Heart Disease).

World Health Organization Group 2 PH Secondary to Left-Sided Heart Disease

Up to three quarters of patients with end-stage CHF exhibit some degree of PH and right ventricular dysfunction, and one-third to one-half have moderate to severe or "fixed" PH unresponsive to vasodilator or inotroph challenge. Pharmacologic challenge has generally included some combination of inotropes (dobutamine, dopamine, milnirone), non-specific vasodilators (nitroglycerin, sodium nitroprusside [SNP]) and/or partially or completely selective pulmonary vasodilators (prostacyclin, prostacyclin analogues, prostaglandin El, sildenafil, inhaled NO) administered pre- or post-LVAD implantation or orthotopic heart transplant. The chronically failing left ventricle increases left atrial and pulmonary venous pressure which increases pulmonary artery pressure (PAP) and right ventricular afterload. With chronic stress, the pulmonary vasculature remodels, resulting in an increased PVR that further increases PAP out of proportion to the increased pulmonary venous pressure leading to an increase in trans-pulmonary pressure gradient (TPG) in approximately one-third or more of advanced CHF patients. However, the extent to which this increased PVR and TPG is mediated by tonic (and hence acutely reversible) compensatory pulmonary vasoconstriction versus relatively fixed structural vascular remodeling, and the degree to which each of these components is ultimately reversible in advanced CHF is often difficult to predict based on previously known methods. As the key intermediary between right ventricular output and left ventricular preload, the dynamic status of the pulmonary vasculature in patients with chronic CHF before, during and after LVAD placement is both highly complex and critically important to clinical outcome. PH unresponsive to pharmacological therapy has been associated with an increased risk of right heart failure and overall poor prognosis following orthotopic heart transplant, and is considered to be a contraindication for that procedure. In contrast, the predictive power of preoperative hemodynamic attributes of PH for the development of post-LVAD right heart failure is complex. Indeed, both low pre-implantation PAP (perhaps indicative of poor right ventricular contractility) and high pre-implantation PVR have been reported to be predictive of the subsequent development of post-LVAD right heart failure. The presence of fixed PH in end-stage CHF is now considered to be an indication for LVAD therapy versus a contraindication for heart transplant, based in part on the consistent observation that chronic unloading of the left ventricle by a well-functioning LVAD over time reverses "fixed" Group 2 PH in CHF patients in whom PH had been otherwise unresponsive to pharmacological intervention before LVAD implantation, thus rendering these patient eligible for heart transplant. Maximum improvement in PH status appears to be reached within the first 6 months of LVAD support, and remain stable thereafter. Thus, although the LVAD-treated end-stage CHF population will likely become preferentially enriched in patients with WHO Group 2 PH targeting bridge-to-transplant, destination therapy or even bridge-to-recovery, the importance of avoiding LVAD-related adverse events, which are associated with poorer post-heart transplant prognosis, has recently been emphasized .

Interventricular Interactions and Right Heart Failure after LVAD Implantation

Although the beneficial effects of continuous-flow LVADs on survival and quality-of-life as well as WHO Group 2 PH have been well documented, the direct and indirect effects of these devices on right ventricular function have only recently been evaluated in detail. The same SVI and DVI operative in non-LVAD-supported CHF may also play a clinically and therapeutically important role in post-LVAD right heart failure. The implanted LVAD actively increases left ventricular outflow which decompresses the left ventricle, thereby decreasing pulmonary vascular congestion and reducing right ventricular afterload; however the same augmented LVAD outflow increases right ventricular preload which may overwhelm the functional capacity of the previously stressed and/or damaged right ventricle. The decompression of the left ventricle also resets SVI and DVI. Current post-operative hemodynamic LVAD management primarily targets restoration of normal systemic peripheral end-organ (e.g. renal and hepatic) perfusion (as measured by CI) in order to permit gradual weaning of inotropic agents and diuretics. Fluid therapy is generally targeted to maintain initial pump speed >2 liters/min with a right atrial filling pressure <20 mm Hg). After hospital discharge, attributes of pulmonary vascular congestion and PH and the need for inotropic pharmacological support generally decline as measures of peripheral end-organ perfusion progressively improve gradually over a period of days to weeks. Despite initial reductions in pulmonary vascular congestion, PH and excessive right ventricular afterload (which together should improve right ventricular function), right ventricular dysfunction as assessed by transthoracic echocardiogram may remain impaired for up to 3 months following successful LVAD implantation (although more rapid improvement has been reported in stable LVAD patients not requiring inotropic support). The still-weakened right ventricle may be unable to accommodate the increased forward flow generated by the LVAD-assisted left ventricular output, posing a continuing risk of right heart failure. The associated elevation of right arterial pressure one month post-LVAD implantation is linked with impaired exercise tolerance as reliably assessed by the distance walked in six minutes (6MWD) and is predictive of increased mortality risk. Persistent post-LVAD right ventricular dysfunction may reflect diminished intrinsic ability of the right ventricle to undergo self-repair and/or the fact that therapeutic hemodynamic adjustments prioritize the systemic circulation leaving the still-weakened right ventricle exposed to non-optimized hemodynamic stresses.

Post-Operative Management and Adjustment of LVADs

Both the intrinsic right ventricle and the implanted LVAD are preload-dependent and afterload-sensitive, and adequate but not excessive preload of the right ventricle is important to maintain adequate left ventricle/LVAD filling without excessive right ventricular volume overload in the immediate post-operative period. LVAD flows must be kept low enough to avoid right ventricular volume overload but high enough to sustain adequate end-organ perfusion. Inotropes, e.g. milrinone, dobutamine and epinephrine, used to wean from CPB are often continued for days after implantation. Nitroglycerin, SNP, nesiritide and sildenafil have been used to lower. Inhaled NO and prostacyclin have also been used to reduce PVR in order to do so without compromising systemic perfusion. Nevertheless, depending upon the setting of the continuous-flow LVAD rotational speed, right ventricular outflow through the pulmonary circulation may be inadequate to reliably fill the left ventricle, resulting in the development of negative pressure in the left ventricle. This negative left ventricular pressure not only compromises LVAD function, but also draws the interventricular septum leftward, disrupting SVI and essentially eliminating any septal contribution to right heart contractility, further reducing right ventricular outflow. This occurrence can precipitate severe right ventricular dysfunction and overt clinical right ventricular failure, which may decrease LVAD preload further impairing its function thereby causing worsening heart failure. In the intra-operative setting during LVAD implantation, trans-esophageal echocardiography (TEE) continuously monitors the position of the interventricular septum during LVAD adjustment and weaning from CPB; this is particularly important to monitor and manage the acute effects of CPB-withdrawal on the dynamic status of the pulmonary vasculature, which can produce severe acute intra-operative or pen-operative PH. Sub-acute post-operative right ventricular failure secondary to interventricular septal deviation and dysfunction is suspected when transthoracic echocardiography (TTE) reveals a dilated right ventricle accompanied by a small left ventricle and an aortic valve which remains closed due to negative left ventricular pressure. During the post-operative hospitalization, averaging 6 ICU and 20 total inpatient days, periodic TTE assessment of interventricular septal deviation predicts right ventricular failure and guides LVAD rotational speed adjustment to minimize leftward interventricular septal deviation and the consequent risk of right ventricular dysfunction and right ventricular failure. For example, a "ramped speed study" under TTE monitoring may be used to adjust the optimal pump speed taking into account changes in ventricular dimensions, displacement of the interatrial and interventricular septa, and the frequency of aortic valve opening as well as evidence of inadequate left ventricular preloading and right ventricular dysfunction. This TTE-directed optimization may be especially important in patients with poor 6MWD. Reduction of LVAD speed to optimize right ventricular function and/or manage post-LVAD right ventricular failure may require temporary reintroduction of inotropic pharmacological support and/or intravenous vasodilators to maintain adequate systemic end-organ perfusion. Despite these intensive measures, right ventricular failure remains a leading cause of early mortality after implantation of even the most modern continuous-flow LVADs. Furthermore, current approaches to optimize LVAD, right arterial and right ventricular hemodynamics with inotropic support and/or conventional intravenous vasodilators is limited by the fact that these agents may induce arrhythmias and/or systemic hypotension, increase oxygen demand, and worsen oxygenation due to pulmonary ventilation-perfusion mismatching, leaving ample room for new approaches that would optimize LVAD function and reduce the risk of right ventricular failure while avoiding these serious pharmacologic side effects. Furthermore, other therapeutic approaches may be needed to enable right ventricular outflow through the pulmonary circulation to maintain sufficient left ventricular preload to adequately fill the LVAD-assisted left ventricle at LVAD settings sufficient to maintain adequate end-organ perfusion during the critical post-implantation period.

Pulmonary Vasodilators in the Management of Patients with Left Ventricular Assist Devices Acute pulmonary vasoreactivity testing (AVT) by right heart catheterization with selective pulmonary vasodilators such as inhaled NO is routinely performed in other forms of PH such as pulmonary arterial hypertension (PAH, or WHO Group 1 Pulmonary Hypertension). AVT with inhaled NO is only rarely and cautiously performed in non-LVAD-supported patients with CHF prior to heart transplantation, because acute highly-selective reduction in PVR and right ventricular afterload may overload the failing left ventricle thereby increasing right arterial and pulmonary venous pressure, potentially precipitating acute pulmonary edema. Instead, "fixed" versus "reversible" PH in advanced CHF is usually interrogated by the hemodynamic response or lack thereof to combinations of systemically-administered non-pulmonary-specific vasodilators such as SNP, nitroglycerin or adenosine and inotropic agents administered acutely, or in some studies, for over 72 hours. At times, acute or longer infusion of highest tolerated doses (i.e. free of systemic hypotension or other systemic side effects) of prostacyclin and prostaglandin $E_1$ in conjunction with inotropes or non-specific vasodilators have been used for PH-reversibility in this setting. Inhaled or intravenous prostanoids may be currently considered preferable to inhaled NO in non-LVAD-supported CHF patients in some but not all geographies despite significant decreases in systemic vascular resistance (SVR) and the clear demonstration that chronic intravenous prostacyclin therapy increases mortality in patients with end-stage CHF.

Because early extubation, removal of monitoring lines and ambulation are recommended, TTE becomes a primary tool to aid in the regulation of LVAD settings and hemodynamic fluid and pharmacological therapy in the post-acute post-implant setting. Management is complicated by the fact that right ventricular and both the pulmonary and systemic circulations are simultaneously undergoing complex dynamic interactions and adaptations to the newly functioning LVAD and the fact that most vasoactive drugs affect both circulatory systems simultaneously, e.g. SNP dilates both systemic and pulmonary resistance vessels. The high pulmonary selectivity and very short half-life of inhaled NO are ideal attributes to classify, manage and optimize the pulmonary vascular status in CHF patients on LVAD support, and to optimize LVAD performance in this setting. In the post-operative period, once the acute effects of CPB-induced PH have abated and the patient stabilized on a hemodynamic regimen, AVT with inhaled NO under echocardiographic and/or right heart catheterization guidance could be used to determine if inhaled NO should be continued in order to adjust left ventricular preload to optimize SVI and LVAD performance and reduce the risk of perioperative and post-operative acute right ventricular dysfunction and right ventricular failure. Specifically, doses of inhaled NO would be titrated against the right ventricular performance including measures of SVI and LVAD rotational speed, power and flow, until the correct combination is achieved to normalize/optimize right ventricular function, SVI, cardiac output, pulsatility and other hemodynamic parameters. In those patients in who CI or LVAD or right ventricular performance appears to benefit, inhaled NO would be continued during the taper of inotrope and/or intravenous systemic vasodilators. These parameters would then be re-monitored with echocardiographic assessment to maintain optimal settings during the post-acute recovery period. It would he anticipated that the provision of critical right ventricular afterload reduction and left ventricular preload enhancement during this period would permit increased CI with less LVAD power, improve pulse index, improve peripheral perfusion and exercise tolerance, and hasten and improve early cardiac rehabilitation, as well as reduce the risk of right heart failure. Additionally, the post-acute response to inhaled NO could be highly predictive of the likelihood of subsequent maximum resolution of residual PH over 6-months resulting from chronic CHF, particularly in those patients whose PH may have been characterized preoperatively as "fixed" by lack of response to the combination of inotropic agents and systemic vasodilators, as the effectiveness of these agents is often tolerability-limited. Thus, inhaled NO could represent a new paradigm in the optimal management of patients with functioning LVADs over the days, weeks and months following implantation.

New Indications Relating to the Use of Inhaled NO with LVADs

In view of the above, aspects of the present invention provide for the utilization of inhaled NO as adjunctive therapy post-LVAD implantation. The inhaled NO therapy may be commenced pre-operatively pre-implantation or intra-operatively before, during or directly after implantation; such inhaled NO therapy may be continued beyond the time period in which it is clinically required in order successfully counteract the acute and temporary PH that occurs as a direct consequence of the CPB procedure itself. Alternatively, inhaled NO could be instituted (or re-instituted) after successful weaning from CPB and the direct consequence thereof In various aspects of the present invention, inhaled NO would thusly be utilized for one or more novel applications to predict and prevent the development of right ventricular failure post successful weaning from CPB in LVAD recipients. As discussed above, right ventricular failure after institution of LVAD support may be consequent to the development or persistence of PH, further impairment of right ventricular contractility secondary to alterations in WI and DVT or other ventricular interactions between the RV and the "unloaded" left ventricle, or further intrinsic impairment of right ventricular contractility given the known susceptibility of the right ventricle to myocardial preservation injury during CPB. Differentiation among these contributing causes is important since they would be managed differently.

One aspect of the present invention provides a method to predict which post-implantation LVAD patients with PH are likely to resolve their PH with continued LV unloading by a functional LVAD. Those patients exhibiting a significant acute reduction in TPG and/or mPAP and/or PVR and/or other measures such as the difference between dPAP and PCWP with inhaled NO would be those more likely to resolve their increased TPG and/or mPAP and/or PVR following LVAD treatment, e.g. after several months of LVAD treatment.

When acute vasoreactivity testing (AVT) is performed pre-LVAD implantation, the PAP is a combination of increased pulmonary vascular resistance and elevated post-capillary pressure measured as either PCWP or right arterial pressure (RAP). The PCWP and RAP effect would be removed once the LVAD is in place, making the AVT results more clearly related to pulmonary vascular resistance, not confounded by increased PCWP and RAP. Accordingly, this aspect of the present invention provides an enhanced predictive tool by performing the AVT after LVAD implantation.

In various embodiments of this aspect, the method comprises measuring one or more pulmonary hemodynamic parameters of a patient with an LVAD to obtain a first pulmonary hemodynamic value; after obtaining the first pulmonary hemodynamic value, administering inhaled NO to the patient with the LVAD; and measuring one or more pulmonary hemodynamic parameters of the patient during or after the inhaled NO administration to obtain a second pulmonary hemodynamic value. A significant improvement in the pulmonary hemodynamic parameter from the first pulmonary hemodynamic value to the second pulmonary hemodynamic value, for example a decrease of at least 10 mm Hg and/or at least 20% can indicate that the patient is likely to resolve the pulmonary hypertension after continued use of the LVAD.

In some embodiments of this aspect, the inhaled NO is administered at a concentration of 5 to 80 ppm for at least 10 minutes. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 10 minutes, about 15 minutes, about 20 minutes, about 25 minutes, about 30 minutes, about 35 minutes, about 40 minutes, about 45 minutes, about 50 minutes, about 55 minutes, and about 60 minutes Exemplary pulmonary hemodynamic parameters include mean pulmonary artery pressure (mPAP), transpulmonary gradient (TPG) and pulmonary vascular resistance (PVR). The one or more pulmonary hemodynamic parameters may be measured by any appropriate procedures, such as by performing a right heart catheterization.

Other known methods of performing acute vasoreactivity testing (AVT) with inhaled NO may also be used in addition to or as an alternative to the methods described above with respect to this aspect of the invention, provided that such AVT is performed after LVAD implantation.

In one or more embodiments of this aspect, the method further comprises placing the patient on a heart transplant list if the decrease in the pulmonary hemodynamic parameter from the first pulmonary hemodynamic value to the second pulmonary hemodynamic value is at least 10 mm Hg and/or at least 20%. In some embodiments, the method further comprises explanting the LVAD and implanting a donor heart in the patient.

As an alternate to the above thresholds of 10 mm Hg and/or 20%, other significant decreases in the pulmonary hemodynamic parameter may be at least 5 mm Hg, at least 6 mm Hg, at least 7 mm Hg, at least 8 mm Hg, at least 9 mm Hg, at least 15 mm Hg, at least 20 nun Hg, or at least 25 mm Hg, and/or at least 5%, at least 10%, at least 15%, at least 25%, at least 30%, at least 35%, at least 40% or at least 50%.

Another aspect of the present invention provides a method to use administration of inhaled NO during the adjustment and setting of the LVAD parameters and hemodynamic pharmacotherapy and fluid replacement therapy once the acute effects of prior CPB on pulmonary hemodynamics have elapsed.

One current methodology of setting an LVAD involves setting the revolutions/min (rpm) rate of an LVAD (such as a HeartMate II LVAD (HM II)) to provide adequate cardiac output and achieve optimal left ventricular decompression, while maintaining a pulsatility index (defined as the maximum LVAD flow rate minus the minimum LVAD flow rate divided by the average LVAD flow rate) of 3.5 to 4. Although modern "continuous-flow" LVAD devices do not themselves have valves that open and close to generate pulsatile flow, the flow rate through these devices at any device setting varies depending upon the pressure gradient between the left ventricle and the aorta such that the increased systolic pressure with each contraction of the left ventricle transiently increases flow through the LVAD creating some pulsatile variation in blood flow. In addition, the fixed-rate speed of a continuous-flow LVAD is usually adjusted to maximize left ventricular decompression and to improve cardiac output, while simultaneously allowing for a minimum aortic valve opening ratio of 1:3 (i.e. the left ventricular systolic pressure achieves a sufficiently high pressure relative to aortic pressure to permit opening of the aortic valve once out of every three systoles despite the continuing efflux of blood through the LVAD).

Another current methodology of setting an LVAD involves optimizing the rpm speed, both hemodynamically and echocardiographically, at the time of LVAD placement, before the patient is discharged from the hospital (i.e., after admission for LVAD placement) and if clinical events such as new symptoms or suction events warranted further adjustment. However, these hemodynamic and echocardiographic assessments used to adjust LVAD settings are static in that they are performed at the left ventricular preload exhibited by the patient at the time and condition under which the test is performed (usually at rest).

The use of inhaled NO during part of the test procedure to maximally relax the pulmonary vessels and lower PVR would provide information on the maximal left ventricular preload that the right ventricle is able to generate unfettered by acutely-reversible pulmonary vasoconstriction. Such dynamic (rather than static) assessment would provide additional information to optimize any particular group of settings of the LVAD to produce the desired cardiac out and pulsatility parameters while avoiding the generation of left ventricular suction as determined by simultaneous TTE. The novel use of inhaled NO as an adjunct to adjusting LVAD parameters should improve the efficiency and safety of functioning LVADs, which should result in improved cardiac output, pulsatility indices and exercise tolerance, and reduce the risk of right heart failure.

As the above prior methods simply understand the extent to which LVAD and right ventricular settings and read-outs reflect the current level of PH without dissecting PH into fixed versus reversible by dynamic testing, these methods limit the range of options within which LVAD function would have to operate efficiently during the recovery period post-LVAD implantation. Accordingly, the more effective and accurate adjustment in LVAD parameters provided by this aspect of the invention can result in improved LVAD efficiency, cardiac output, end-organ perfusion, and exercise tolerance, and retesting with this paradigm and periodically re-setting LVAD parameters can hasten full recovery.

Accordingly, this aspect of the present invention relates to a method of optimizing the settings of an LVAD by utilizing inhaled NO. In various embodiments of this aspect, the method comprises administering inhaled NO to a patient having an LVAD; performing an echocardiogram or similar functional hemodynamic or cardiac imaging assessment on the patient during the administration of inhaled NO; and adjusting or setting one or more parameters of the LVAD during the echocardiogram and during the administration of inhaled NO. In one or more embodiments, adjusting or setting the LVAD parameters during administration of NO helps to optimize cardiac output, end-organ perfusion, LVAD efficiency and/or exercise tolerance.

In one or more embodiments of this aspect, adjusting or setting one or more parameters of the LVAD comprises one or more of (i) determining a low pump speed setting for the LVAD based on the minimal pump speed necessary for the patient's aortic valve to open with each heart beat or (ii) determining a high speed setting for the LVAD based for example on the pump speed at which the septum of the patient's heart flattens.

In some embodiments of this aspect, the inhaled NO is administered at a concentration of 5 to 80 ppm for at least 10 minutes. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1.5 hours, about 2 hours, about 2.5 hours and about 3 hours.

In some embodiments, the LVAD settings are changed over a series of incremental adjustments. For example, the LVAD pump speed may be adjusted upwards in two or more steps. One or more or all of these steps may be performed during the administration of inhaled NO as described herein.

Another aspect of the present invention provides for long-term use of inhaled NO after LVAD implantation. In one or more embodiments of this aspect, if AVT favorably predicts that PH will resolve after continued use of the LVAD, and/or if the settings and read-out and/or the TTE indicate more efficacious LVAD function and hemodynamic status under inhaled NO challenge, then the treating physician may wish to continue administering inhaled NO to the patient continuously for all or part of the convalescent period. In various embodiments, inhaled NO would be administered to the patient during all or part of the day over a period of days, weeks or months to maintain the favorable LVAD function and/or hemodynamic status. Periodic testing may be performed as described above both on and off inhaled NO for a short period of time, such that when sufficient recovery had occurred so that inhaled NO was no longer producing and hemodynamic or TTE change, the patient may be carefully weaned from inhaled NO. This treatment would be expected to result in improved cardiac output and exercise tolerance more quickly, and reduce the risk of right heart failure.

In various embodiments of this aspect, the method comprises administering inhaled NO to a patient with an LVAD for at least 12 hours a day for at least 10 days. The inhaled NO may be administered for several days to many months or even longer. Exemplary treatment times include 10 days, 15 days, 20 days, 25 days, 30 days, 35 days, 40 days, 45 days, 2 months, 3 months, 4 months, 5 months, 6 months, 7 months, 8 months, 9 months, 10 months, 11 months, 1 year, 1.5 years, or 2 years. In some embodiments, the patient is administered inhaled NO indefinitely.

In some embodiments of this aspect, the inhaled NO is administered at a concentration of 5 to 80 ppm for at least 12 hours a day. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 12 hours a day, about 14 hours a day, about 16 hours a day, about 18 hours a day, about 20 hours a day, about 22 hours a day, or up to 24 hours a day.

Due to the fact that a patient with an LVAD had preexisting left ventricular dysfunction, it may be important to ensure that the LVAD is properly functioning prior to administering inhaled NO. Accordingly, in some embodiments, the method further comprises confirming that the LVAD is functioning properly before administering inhaled NO.

In one or more embodiments, the inhaled NO is administered after a patient has been weaned from cardiopulmonary bypass (CPB).

As an alternative to a constant concentration of NO, the dose of NO may be prescribed based on the patient's ideal body weight (IBW). Exemplary NO doses may be in the range of about 25 to about 150 μg/kg IBW/hr, such as about 25, about 30, about 35, about 40, about 45, about 50, about 60, about 70, about 80, about 90, about 100, about 110, about 120, about 130, about 140 or about 150 μg/kg IBW/hr.

In one or more embodiments, the method further comprises monitoring one or more output parameters of the LVAD and/or one or more hemodynamic parameters of the patient, comparing the one or more output parameters and/or the one or more hemodynamic parameters to a predetermined range, and adjusting the dose of inhaled NO if the one or more outputs parameters and/or the one or more hemodynamic parameters are outside of the predetermined range. In some embodiments, the method further comprises providing an alert if the one or more output parameters and/or the one or more hemodynamic parameters are outside of the predetermined range. The inhaled NO dose may be adjusted automatically (e.g. by the NO delivery device or a control system in communication with the NO delivery device), or may be manually adjusted by a physician or other user, such as in response to an alert.

Examples of LVAD parameters that may be monitored include, but are not limited to, pump speed (e.g. rpm), pump flow (e.g. L/min), pump power, pulsatility index, battery level, and LVAD status (e.g. operational, presence or absence of warnings).

In some embodiments, the LVAD has a minimum and/or maximum pump speed that is set by the physician, and can be specific for the individual patient. Alternatively or additionally, the LVAD may also have a minimum and/or maximum pump speed set by the manufacturer of the LVAD. Regardless of whether the minimum and/or maximum pump speed is set by a physician or the manufacturer, exemplary minimum pump speeds include 100 rpm, 200 rpm, 300 rpm, 400 rpm, 500 rpm, 6000 rpm, 700 rpm, 800 rpm, 900 rpm, 1,000 rpm, 1,500 rpm, 2,000 rpm, 2,500 rpm, 3,000 rpm, 4,000 rpm, 5,000 rpm, 6,000 rpm, 7,000 rpm, 8,000 rpm, 9,000 rpm, 10,000 rpm, 11,000 rpm, 12,000 rpm, 13,000 rpm, 14,000 rpm and 15,000 rpm, and exemplary maximum pump speeds include 1,000 rpm, 1,500 rpm, 2,000 rpm, 2,500 rpm, 3,000 rpm, 4,000 rpm, 5,000 rpm, 6,000 rpm, 7,000 rpm, 8,000 rpm, 9,000 rpm, 10,000 rpm, 11,000 rpm, 12,000 rpm, 13,000 rpm, 14,000 rpm, 15,000 rpm, 20,000 rpm and 30,000 rpm. The minimum and maximum pump speeds may depend on the design of the LVAD.

Similarly, in some embodiments, the LVAD has a minimum and/or maximum pump flow that is set by the physician, and can be specific for the individual patient. Alternatively or additionally, the LVAD may also have a minimum and/or maximum pump flow set by the manufacturer of the LVAD. Regardless of whether the minimum and/or maximum pump flow is set by a physician or the manufacturer, exemplary minimum pump speeds include 1 L/min, 1.5 L/min, 2 L/min, 2.5 L/min, 3 L/min, 3.5 L/min, 4 L/min, 4.5 L/min, 5 L/min, 6 L/min, 7 L/min, 8 L/min, 9 L/min and 10 L/min, and exemplary maximum pump flows include 3 L/min, 3.5 L/min, 4 L/min, 4.5 L/min, 5 L/min, 6 L/min, 7 L/min, 8 L/min, 9 L/min, 10 L/min, 11 L/min, 12 L/min, 13 L/min, 14 L/min and 15 L/min. The minimum and maximum pump flows may depend on the design of the LVAD.

In some embodiments, the pulsatility index of the LVAD has a minimum and/or maximum threshold. As explained above, the pulsatility index is the maximum pump flow minus the minimum pump flow, divided by the average pump flow. As the pulsatility index is an indication of how much support the LVAD is providing to the heart (a higher pulsatility index indicates that the LVAD is providing more support), high pulsatility indices can be a cause of concern. Accordingly, exemplary maximum pulsatility indices include values of 5, 6, 7, 8, 9, 10, 11, 12, 13, 14, 15 or 20.

In some embodiments, the battery level of the LVAD is monitored. As a low battery can indicate a future or imminent shutdown of the LVAD, when the battery level of the LVAD drops below a certain threshold, the inhaled NO dose may be lowered, a weaning protocol may be initiated, and/or an alert is provided. Examples of minimum battery levels include 30%, 25%, 20%, 15%, 10%, 9%, 8%, 7%, 6%, 5%, 4%, 3%, 2% or 1% battery remaining or 6 hours, 5 hours, 4 hours, 3 hours. 2 hours, 1 hour, 30 minutes, 20 minutes, 15 minutes, 10 minutes, 5 minutes, 4 minutes, 3 minutes, 2 minutes or 1 minute of battery life remaining.

Similarly, other indicators of LVAD malfunction or complete LVAD failure may be monitored, and the inhaled NO dose may be adjusted, a weaning protocol may be initiated and/or an alert may be provided. Again, the inhaled NO dose may be adjusted automatically (e.g. by the NO delivery device or a control system in communication with the NO delivery device), or may be manually adjusted by a physician or other user.

Another aspect of the present invention relates to a method of monitoring the left ventricle of a patient with an LVAD. In various embodiments of this aspect, the method comprises reducing the pump speed of the LVAD or turning off the LVAD; measuring one or more pulmonary hemodynamic parameters of the patient to obtain a first pulmonary hemodynamic value; preloading the left ventricle by administering inhaled NO to the patient; and measuring one or more pulmonary hemodynamic parameters of the patient after or during administration of inhaled NO to obtain a second pulmonary hemodynamic value. In some embodiments, the pulmonary hemodynamic parameter is selected from LAP, PCWP and CO, or may be any assessment of the left ventricular reserve to compensate for increased left ventricular preload that can be measured through right heart catheterization, echocardiographic, MRI or other techniques.

In some embodiments of this aspect, the inhaled NO is administered at a concentration of 5 to 80 ppm for at least 10 minutes. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1.5 hours, about 2 hours, about 2.5 hours, about 3 hours, about 3.5 hours, about 4 hours, about 5 hours, about 6 hours, about 7 hours or about 8 hours.

According to one or more embodiments, an increase in LAP and/or PCWP from the first pulmonary hemodynamic value to the second pulmonary hemodynamic value of less than 5 mm fig indicates that the left ventricle is improving. Other exemplary values that indicate an improvement in the left ventricle include an LAP and/or PCWP increase of less than 1 mm Hg, 2 mm Hg, 3 mm Hg, 4 mm Hg, 6 mm Hg, 7 mm Hg, 8mm Hg, 9 mm Hg, 10 mm Hg, 11 mm Hg, 12 mm Hg, 13 mm Hg, 14 mm Hg or 15 nom Hg. In some embodiments, the method further comprises modifying treatment if the left ventricle is improving, such as explanting the LVAD from the patient. Other modifications in treatment can include changing the supportive medication (e.g. diuretics and/or inotropic medications) that the patient is given, such as reducing the supportive medication.

Another aspect of the present invention relates to a method of exercising a heart of a patient having an LVAD. In various embodiments of this aspect, the method comprises reducing and/or modulating the pump speed of the LVAD or turning off the LVAD; preloading the left ventricle by administering inhaled NO to the patient for at least 5 minutes; discontinuing the inhaled NO administration; and repeating the preloading and discontinuation to exercise the left ventricle of the patient's heart.

In some embodiments of this aspect, the inhaled NO is administered at a concentration of 5 to 80 ppm for at least 5 minutes. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1.5 hours, about 2 hours, about 2.5 hours, about 3 hours, about 3.5 hours, about 4 hours, about 5 hours, about 6 hours, about 7 hours or about 8 hours.

The preloading of the left ventricle may be performed multiple times per day, such as twice a day, three times a day, four times a day, five times a day, six times a day, seven times a day, eight times a day, nine times a day or ten times a day. Alternatively, the preloading may be performed once a day. If the preloading is performed multiple times per day, the preloading procedures may be clustered together (e.g. spaced apart by several minutes or a couple hours) or may be spread out throughout the day. The preloading of the left ventricle may also be performed once a week, two days a week, three days a week, four days a week, five days a week, six days a week, or seven days a week. In exemplary embodiments, the left ventricle is preloaded several times a day for several days a week, such as two to five times a day for two to four days a week or other combinations of the above daily and weekly preloading schedules.

In some embodiments, the first instance or first few instances of the exercising of the patient's left ventricle is performed under the direct supervision of a physician, but once an appropriate exercise protocol has been determined for a patient, then the exercise protocol may be performed under patient control or may be automated by the NO delivery device and/or control system.

Another aspect of the present invention relates to a method of reducing the risk of adverse events during LVAD use. In particular, it is believed that inhaled NO can improve cardiovascular function of LVAD recipients with functioning LVADs, reduce the risk of adverse events associated with continuous-flow or semi-pulsatile LVADs (e.g thrombosis, gastrointestinal bleeding) and improve the function of transplanted hearts by making the cardiovascular system more compliant.

A specific deficiency in continuous-flow LVADs is that the reduced pulsatility of peripheral perfusion generated by these devices compared to pulsatile-flow LVAD devices and/or the normal circulation derived from a well-functioning human heart as measured by pulsatility index, pulse pressure and/or the frequency of opening of the aortic valve has been implicated in a number of adverse events including reduced peripheral vascular compliance, gastrointestinal bleeding, arteriovenous malformations, hemolysis, pump thrombosis, aortic insufficiency and lower rate of recovery of left ventricular function. These adverse events can also be associated with semi-pulsatile LVADs.

Evidence of deranged microvascular function following continuous-flow LVAD support has been documented by several sensitive techniques evaluating post-ischemic autoregulation of blood flow, including flow-mediated dilation (FMD) of the brachial artery and the reactive hyperemic index (RHI), both of which has been shown to be predominantly mediated by locally released NO.

While not wishing to be bound by any particular theory, it is believed that diminished LVAD-generated pulsatility is linked to derangement of NO-mediated vascular autoregulatory function because pulsatile flow is considered the key generator of microvascular directional shear stress at the level of the microvascular endothelial cell that is strongly implicated in the autoregulation of NO biology in the vascular system. Thus, it is believed that at least some of the adverse events associated with continuous-flow LVAD's and their reduced pulsatility could be secondary to impaired NO-mediated autoregulatory vascular function.

Shear stress, and hence pulsatility, is a key factor in adapting organ perfusion to changes in cardiac output presumably in part through regulation of NO. Deranged NO-mediated autoregulatory vascular function is reflected not only in peripheral vessels but also in coronary vessels as well, including an association with a higher rate of in-stent thrombosis following percutaneous coronary intervention. It is believed that impaired NO-mediated coronary vascular autoregulation could provide a potential mechanism that would contribute to reduced LV recovery during continuous-LVAD support. NO not only mediates autoregulation of vascular tone, but also modulates platelet activation and adhesion, such that deranged NO regulation could contribute to the increased thrombosis associated with continuous-flow LVAD support. Attributes of NO-mediated vascular dysfunction are considered to be significant overall risk factors for adverse cardiovascular outcomes in the general population. Indeed, some authors have suggested that impaired endothelial dilation is the ultimate cause of cardiovascular diseases such as coronary artery disease and peripheral artery disease. These widespread effects of NO on vascular health are thought to be mediated in large part by modulating oxidative stress through the control of nitrosylation of a wide range of regulatory proteins.

Inhalational NO could therefore improve endothelial function and vascular health, and thereby important clinical outcomes, in patients on long-term continuous-flow LVAD support, through two related and potentially complementary or synergistic mechanisms. Firstly, as discussed above, inhaled NO, by dilating pulmonary vessels, would increase left ventricular preload and improve left ventricular filling, thereby increasing the frequency of aortic valve opening and closing, and hence pulsatility for any given LVAD speed setting. This effect might be more dominant during periods of rest or sleep, or during periods of increased cardiac output demand such as exercise, depending upon the characteristics of the LVAD device and setting.

Secondly, inhaled NO also has the potential to improve NO-mediated vascular autoregulatory function and health independent of its effect of circulatory pulsatility, by improving NO bioavailability throughout the peripheral and coronary circulation. NO can be generated by NO synthase (NOS) or by the breakdown of nitrite or other compounds to NO. Inhalation of NO for even short periods of time (e.g. two hours) increases the circulating levels of a variety of molecules that have the potential to regenerate NO within the microcirculation including nitrite ($NO_2^-$), nitrate ($NO_3^-$) and S-nitrosohemoglobin. These and other NO-derive molecules have been invoked in the beneficial so-called "distal effects" of inhaled NO. For example, inorganic nitrite is an endogenous substance produced by the oxidation of NO. under aerobic conditions (such as in the lung) but conversely, in acidic conditions such as might be found in ischemic tissues, $NO_2^-$ can be chemically and enzymatically reduced back to NO® where it has favorable effects alleviating some of the consequences of local ischemia including the amelioration of ischemia-reperfusion injury. Thus, inhaled NO is expected to improve and/or sustain the tissue integrity and autoregulation of the peripheral vasculature and the tissues which it supplies, including the myocardium, through a complex cascade of NO-mediated biochemical effects in the setting of endothelial dysfunction that accompanies prolonged continuous-flow LVAD support.

Accordingly, embodiments of the present invention provide for the administration by inhalation of NO at doses and for durations that are expected to (1) improve pulsatility through the NO's direct hemodynamic action on the pulmonary vasculature thereby promoting left ventricular filling, aortic valve opening and closure, and thereby maximize pulsatile flow and/or (2) increase peripheral NO bioavailability through provision NO precursors in the form of NO metabolites such as $NO_2^-$, $NO_3$, nitrosohemoglobin and other that are formed in the lung as a result of NO inhalation and transported by the circulation to peripheral tissues where NO can be reformed further reducing endothelial dysfunction.

In various embodiments of this aspect, the method comprises administering inhaled NO to a patient with an LVAD for at least 12 hours a day for at least 10 days. The inhaled NO may be administered for several days to many months or even longer. Exemplary treatment times include 10 days, 15 days, 20 days, 25 days, 30 days, 35 days, 40 days, 45 days, 2 months, 3 months, 4 months, 5 months, 6 months, 7 months, 8 months, 9 months, 10 months, 11 months, 1 year, 1.5 years, or 2 years. In some embodiments, the patient is administered inhaled NO indefinitely.

In some embodiments of this aspect, the inhaled NO is administered at a concentration of 5 to 80 ppm for at least 12 hours a day. Exemplary inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm. Exemplary NO administration times include about 12 hours a day, about 14 hours a day, about 16 hours a day, about 18 hours a day, about 20 hours a day, about 22 hours a day, or up to 24 hours a day.

Due to the fact that a patient with an LVAD had preexisting left ventricular dysfunction, it may be important to ensure that the LVAD is properly functioning prior to administering inhaled NO. Accordingly, in some embodiments, the method further comprises continuing that the LVAD is functioning properly before administering inhaled NO.

In one or more embodiments, the inhaled NO is administered after a patient has been weaned from cardiopulmonary bypass (CPB).

As an alternative to a constant concentration of NO, the dose of NO may be prescribed based on the patient's ideal body weight (IBW). Exemplary NO doses may be in the range of about 25 to about 150 μg/kg IBW/hr, such as about 25, about 30, about 35, about 40, about 45, about 50, about 60, about 70, about 80, about 90, about 100, about 110, about 120, about 130, about 140 or about 150 µg/kg IBW/hr.

In one or more embodiments, the method further comprises monitoring one or more output parameters of the LVAD and/or one or more hemodynamic parameters of the patient, comparing the one or more output parameters and/or the one or more hemodynamic parameters to a predetermined range, and adjusting the dose of inhaled NO if the one or more outputs parameters and/or the one or more hemodynamic parameters are outside of the predetermined range. In some embodiments, the method further comprises providing an alert if the one or more output parameters and/or the one or more hemodynamic parameters are outside of the predetermined range. The inhaled NO dose may be adjusted automatically (e.g. by the NO delivery device or a control system in communication with the NO delivery device), or may be manually adjusted by a physician or other user, such as in response to an alert.

Examples of LVAD parameters that may be monitored include, but are not limited to, pump speed (e.g. rpm), pump flow (e.g. L/min), pump power, pulsatility index, battery level, and LVAD status (e.g. operational, presence or absence of warnings).

In some embodiments, the LVAD has a minimum and/or maximum pump speed that is set by the physician, and can be specific for the individual patient. Alternatively or additionally, the LVAD may also have a minimum and/or maximum pump speed set by the manufacturer of the LVAD. Regardless of whether the minimum and/or maximum pump speed is set by a physician or the manufacturer, exemplary minimum pump speeds include 100 rpm, 200 rpm, 300 rpm, 400 rpm, 500 rpm, 6000 rpm, 700 rpm, 800 rpm, 900 rpm, 1,000 rpm, 1,500 rpm, 2,000 rpm, 2,500 rpm, 3,000 rpm, 4,000 rpm, 5,000 rpm, 6,000 rpm, 7,000 rpm, 8,000 rpm, 9,000 rpm, 10,000 rpm, 11,000 rpm, 12,000 rpm, 13,000 rpm, 14,000 rpm and 15,000 rpm, and exemplary maximum pump speeds include 1,000 rpm, 1,500 rpm, 2,000 rpm, 2,500 rpm, 3,000 rpm, 4,000 rpm, 5,000 rpm, 6,000 rpm, 7,000 rpm, 8,000 rpm, 9,000 rpm, 10,000 rpm, 11,000 rpm, 12,000 rpm, 13,000 rpm, 14,000 rpm, 15,000 rpm, 20,000 rpm and 30,000 rpm. The minimum and maximum pump speeds may depend on the design of the LVAD.

Similarly, in some embodiments, the LVAD has a minimum and/or maximum pump flow that is set by the physician, and can be specific for the individual patient. Alternatively or additionally, the LVAD may also have a minimum and/or maximum pump flow set by the manufacturer of the LVAD. Regardless of whether the minimum and/or maximum pump flow is set by a physician or the manufacturer, exemplary minimum pump speeds include 1 L/min, 1.5 L/min, 2 L/min, 2.5 L/min, 3 L/min, 3.5 L/min, 4 L/min, 4.5 L/min, 5 L/min, 6 L/min, 7 L/min, 8 L/min, 9 L/min and 10 L/min, and exemplary maximum pump flows include 3 L/min, 3.5 L/min, 4 L/min, 4.5 L/min, 5 L/min, 6 L/min, 7 L/min, 8 L/min, 9 L/min, 10 L/min, 11 L/min, 12 L/min, 13 L/min, 14 L/min and 15 L/min. The minimum and maximum pump flows may depend on the design of the LVAD.

In some embodiments, the pulsatility index of the LVAD has a minimum and/or maximum threshold. As explained above, the pulsatility index is the maximum pump flow minus the minimum pump flow, divided by the average pump flow. As the pulsatility index is an indication of how much support the LVAD is providing to the heart (a higher pulsatility index indicates that the LVAD is providing more support), high pulsatility indices can be a cause of concern. Accordingly, exemplary maximum pulsatility indices include values of 5, 6, 7, 8, 9, 10, 11, 12, 13, 14, 15 or 20.

In some embodiments, the battery level of the LVAD is monitored. As a low battery can indicate a future or imminent shutdown of the LVAD, when the battery level of the LVAD drops below a certain threshold, the inhaled NO dose may be lowered, a weaning protocol may be initiated, and/or an alert is provided. Examples of minimum battery levels include 30%, 25%, 20%, 15%, 10%, 9%, 8%, 7%, 6%, 5%, 4%, 3%, 2% or 1% battery remaining or 6 hours, 5 hours, 4 hours, 3 hours. 2 hours, 1 hour, 30 minutes, 20 minutes, 15 minutes, 10 minutes, 5 minutes, 4 minutes, 3 minutes, 2 minutes or 1 minute of battery life remaining.

Similarly, other indicators of LVAD malfunction or complete LVAD failure may be monitored, and the inhaled NO dose may be adjusted, a weaning protocol may be initiated and/or an alert may be provided. Again, the inhaled NO dose may be adjusted automatically (e.g. by the NO delivery device or a control system in communication with the NO delivery device), or may be manually adjusted by a physician or other user.

Another aspect of the present invention provides a method for optimizing the inhaled NO dose for a continuous-flow or semi-pulsatile LVAD to reduce the risk of adverse events during LVAD use and/or optimize endothelial function.

In some embodiments of this aspect, dosing would be optimized by first optimizing the continuous-flow LVAD settings by conventional means and/or by the additional means described above. Next, endothelial function may be measured, such as by FMD and/or RHI. This adjustment could include the introduction of pulse modulation into the regulation of continuous-flow LVAD use and/or the use of Enhanced External Counter Pulsation Therapy (EECP Therapy) to which could be used in concert with inhaled NO. Inhaled NO would be commenced at one or more doses, for various periods of time, following which endothelial function would be re-measured using the same technique. Inhaled NO dosing would be modified in various stepwise fashions to identify an optimal dosing paradigm to maximize the improvement in endothelial function. Additionally, various NO-related molecules and other biomarkers of endothelial function would be measured in blood or plasma and correlated with the RHI and/or FMD measurement, to provide optimal monitoring of endothelial function to facilitate ongoing dose adjustments. Such correlation may detect and/or determine the optimal parameter to measure to ensure most ideal management of dosing of inhaled NO for the purpose of optimizing and/or individualizing inhaled NO dosing to maximize endothelial function in patients on long-term continuous-flow LVAD support.

In some embodiments of this aspect, the inhaled NO is administered at an initial concentration of 5 to 80 ppm. Exemplary initial inhaled NO concentrations include about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, and about 80 ppm.

As an alternative to a constant concentration of NO, the dose of NO may be prescribed based on the patient's ideal body weight (IBW). Exemplary initial inhaled NO doses may be in the range of about 25 to about 150 µg/kg IBW/hr, such as about 25, about 30, about 35, about 40, about 45, about 50, about 60, about 70, about 80, about 90, about 100, about 110, about 120, about 130, about 140 or about 150 µg/kg IBW/hr.

Exemplary increments for optimizing the inhaled NO dose include adjusting the NO concentration by 0.1 ppm, 0.2 ppm, 0.5 ppm, 1 ppm, 2 ppm, 3 ppm, 4 ppm, 5 ppm, 6 ppm, 7 ppm, 8 ppm, 9 ppm, 10 ppm, 15 ppm and 20 ppm, or 0.1, 0.2, 0.5, 1, 2, 3, 4, 5, 6, 7, 8, 9, 10, 15, 20, 25, 30, 35, 40 or 50 tag NO/kg IBW/hr.

Once the inhaled NO dose is optimized, the NO may be continued to be administered during long-tetra LVAD use, such as described above.

CONTROL SYSTEM

The methods described above may be implemented in one or more devices or systems utilizing a combination of hardware and software. It is understood that a control system as described herein may be a standalone or discrete hardware and software based device which communicates with the LVAD and the NO delivery device, or the control system may be a predominantly software-only implementation resident on the existing LVAD hardware or, the control system may be a predominantly software-only implementation resident on the existing NO delivery device hardware.

In various embodiments, the control system includes appropriate components for transmitting and/or communicating information and/or data between the NO delivery device, the LVAD and the control system. Communication to and from the control system may be over a communication path, where the communication path may be wired or wireless, and wherein suitable hardware, firmware, and/or software may be configured to interconnect components and/or provide electrical communications over the communication path(s). For example, the communication path may be a wireless optical line-of-sight signal (e.g. infrared signal) from one transceiver to another transceiver or from a transmitter to a receiver.

Control System Hardware Architecture

Figure 4:
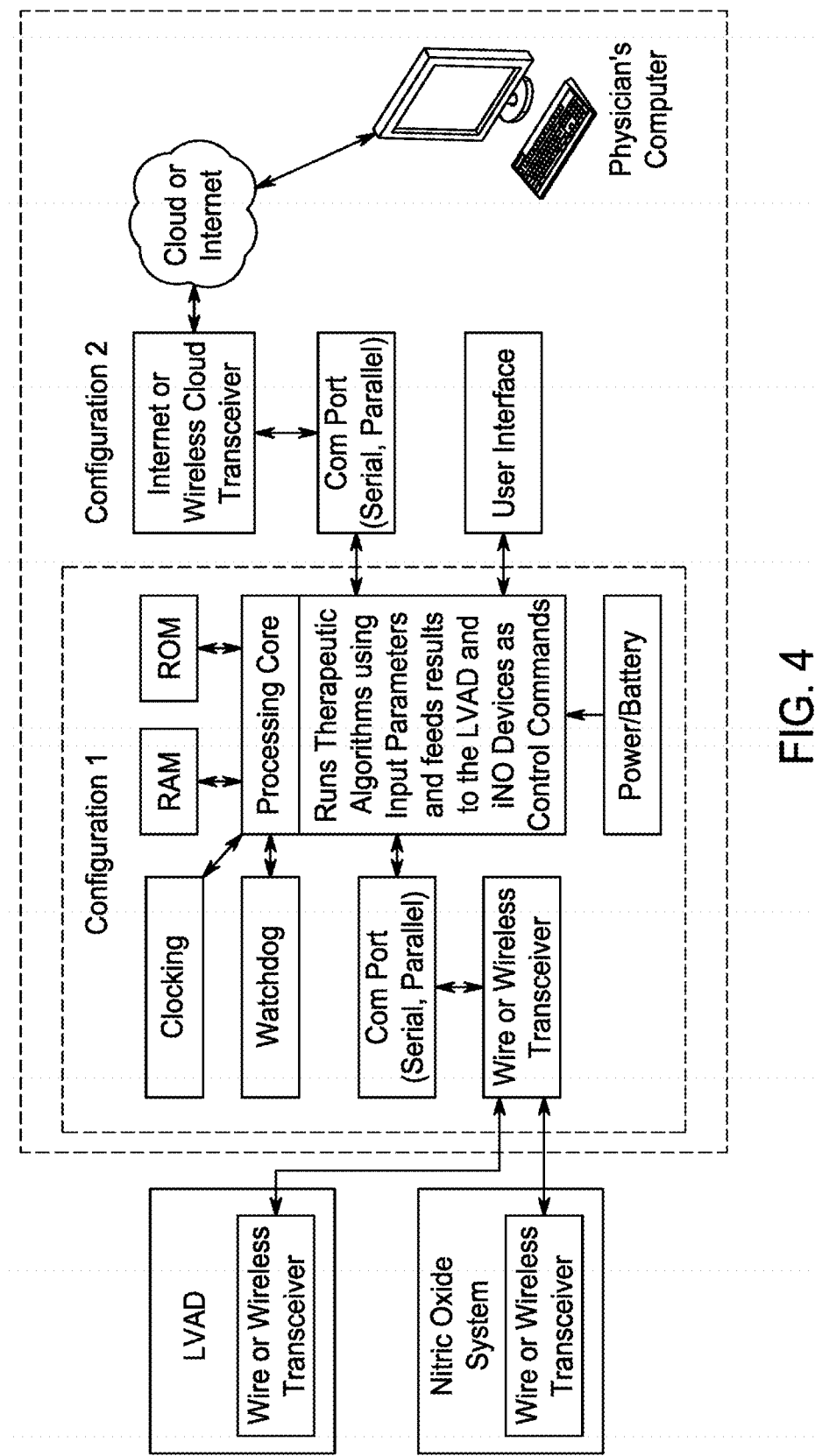
FIG. 4 illustrates an exemplary hardware configuration that can be used in accordance with one or more embodiments of the invention.

Regardless of the integration technique (standalone or integral to the LVAD or NO delivery device), the control system may comprise certain hardware elements as are shown in FIG. 4. Configuration 1 of FIG. 4 includes an exemplary set of hardware elements for the control system. These elements can include a processing core which can be implemented using a microprocessor, a microcontroller, a field-programmable gate array (FPGA) or other digital logic processing device. The control system can also comprise volatile and/or non-volatile memory with the volatile memory allowing for efficient data processing, and the latter being resident to allow for programming of clinical scenarios or algorithms (code) into the invention. Also resident are the processor support functions of clocking (oscillator) as well as a safety watchdog. Two way data communications is provided with both the LVAD and NO delivery devices as noted earlier or simply with the other system if the invention is implemented resident on the LVAD or NO device hardware. A battery or wall power supply is provided to power the electronics and this battery or wall power may be shared with the LVAD or nitric oxide delivery devices.

Configuration 2 of FIG. 4 also provides an exemplary set of hardware elements for the control system, which is a more expansive configuration than Configuration 1. In Configuration 2, data is also exchanged with the internet or cloud in order that a physician can remotely view patient data and remotely make adjustments to the LVAD or NO delivery device. It is understood that analytics specific to embodiments of the invention and/or optimization of treatment protocols may also be provided to the physician remotely (e.g. in the foam of a cloud or internet based application, or as a program resident on the physicians laptop, tablet, smart phone or other device) for patient status tracking or adjustment of treatment regimens. Configuration 2 may also include a user interface for two way information exchange with the patient (or caregiver).

If the control system is implemented integral to the NO delivery device or the LVAD, then many if not all of the hardware elements described above may already be resident on the NO delivery device or on the LVAD.

Control System Input/Output (JO) Hardware

Regardless of whether the control system is standalone or resident on the LVAD or NO delivery device, many of the processing tasks are unaffected and therefore may be equivalent. However, certain tasks such as input/output routines and hardware-level code-interaction-dependent tasks (e.g. addressing of memory) may vary depending on whether the control system is standalone or resident on the LVAD or NO delivery device.

The I/O hardware can include at least one bidirectional data port in the case of the LVAD and N 0 device resident designs and at least two bidirectional data ports in the case of the standalone implementation. It is understood that this bidirectional data port is preferably an opto-isolated serial port; however, other bidirectional data communications schemes including parallel ports, LANs, USB, etc. are also possible. Such bidirectional communications schemes are abundantly described in the art. Further, it is possible that bidirectional communications can be implemented via wireless techniques such as by optical means such as infrared (IR) or by radio frequency (RF) means such as by Bluetooth. Regardless of the communication technique, the bidirectional data transfer preferably occurs in a timely fashion.

Control System Uscr Interface Hardware

For a control system that is resident on the NO delivery device or resident on the LVAD, the user interface can be integrated into the existing, yet extended, user interfaces of those devices. For instance, if the control system is implemented on a NO delivery device, the control system may require additional settings, alarm and modes not currently resident on such a NO delivery device, and therefore the user interface of the NO delivery device can be extended to incorporate such interaction. Further, in the case of a control system that is resident on an LVAD system, the LVAD system user interface can be modified to extend its functionality consistent with new modes, alarms and settings. In addition, many LVAD systems provide for data display on a device worn on the patient and also provide for clinician mediated settings on an ancillary system monitor. It is understood that the functionality of such ancillary system monitor user interfaces can be extended to accommodate the control system.

Finally, in some embodiments of a control system implemented on a standalone device, the user interface can have one of at least two configurations. The first configuration can include an ancillary system monitor which is used by the clinician to set up the system and then removed from the system after setup and initiation of the system. Such a strategy is consistent with the Configuration 1 of FIG. 4. Alternately, a user interface can be integrated into the control system and worn by the user in the form of a module, preferably with a graphical display. Such a strategy is consistent with the more elaborate architecture of Configuration 2 of FIG. 4.

Control System Remote Connectivity Hardware

As shown in FIG. 4, additional functionality may be added to the control system in the form of remote connectivity capability. Hardware for implementing such a strategy may consist of a wired or wireless link to either a computer with an internet link or to a transceiver capable of remote information exchange such as GSM or other remote wireless techniques which can be tied into an internet or cloud infrastructure. It is further understood that this remote information exchange can be implemented using secure/encrypted data links. Other similar techniques are known to those skilled in the art and include, for instance, current bidirectional internet/cloud based secure data exchange schemes such as those based on e.g, Intel's Internet of Things (IoT) architecture and similar emerging architectures. Remote connectivity capability can include a remote application programmed on a computer, a cell phone, smart phone, tablet or other device which receives information from either the internee or from a cloud and which displays this information and allows for bi-directional communication with the control system for many purposes, e.g. settings adjustments.

Control System Software Architecture

The control system can include a software component which asserts itself as the master over the functionality of the resident NO delivery device and/or LVAD controllers. This software component can be responsible for controlling the NO delivery device and LVAD in an integrated fashion consistent with the clinical scenarios outlined above and/or consistent with the user-specified controller functionality specified below.

Master Slave Configuration

Regardless of whether the invention is resident on the NO delivery device, on the LVAD or is standalone, the control system can be capable of operating with the NO delivery device and LVAD in a master/slave configuration. Specifically, the control system can assert a master role when modes of operation are engaged in which the control of the LVAD and NO delivery device are controlled by the control system. This may include removing the option to make settings adjustments on the LVAD or NO delivery device without overriding the master/slave configuration. Such a master/slave configuration can obviate potential control ambiguity resulting from adjustments to two or even three user interfaces. Such a master/slave configuration can be made possible by integrating additional code into the LVAD or NO delivery device allowing for a master/slave configuration, or the master/slave configuration can be implemented by allowing the control system to immediately override any settings changes made to the LVAD or NO delivery device. Finally, the master/slave configuration can be set and overridden by a clinician through the user interface screen of the control system or remotely via a cloud/internet based application or via a resident application on a tablet, smart phone, laptop or other device.

Input/Output Parameters

The control system can utilize certain input parameters from the LVAD and/or the NO delivery device, and the control system can include software functionality which is implemented in such a fashion as to command control of aspects of the LVAD and NO delivery device functionality. Further, a set of output parameters from the control system can be used so that the LVAD and NO delivery device can be commanded to perform certain tasks.

Figure 5:
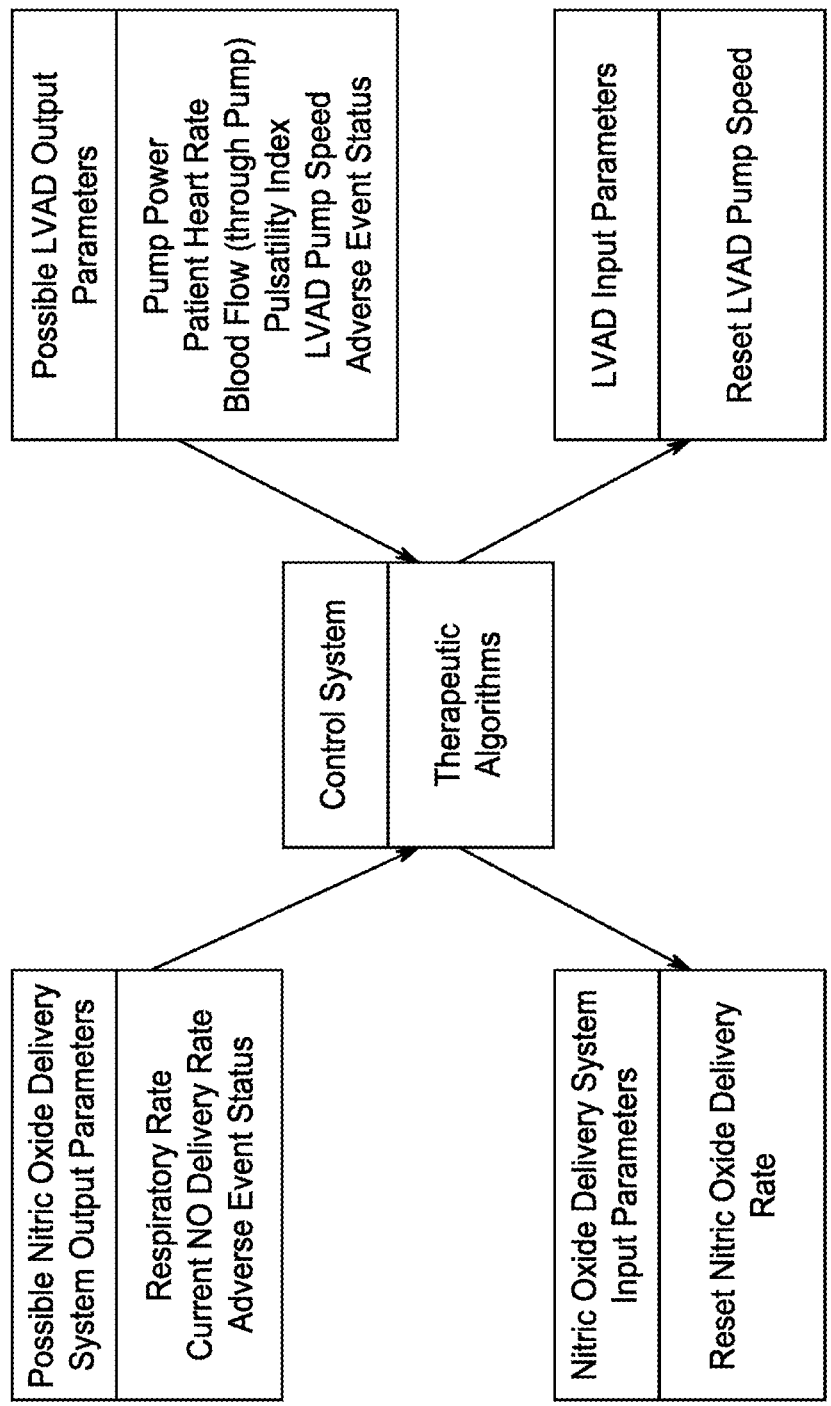
FIG. 5 illustrates exemplary input and output parameters_ that can be used in accordance with one or more embodiments of the invention.

An exemplary set of input and output parameters is shown in FIG. 5. For example, the input parameters from the NO delivery device can include, but are not limited to, the patient's respiratory rate, the current NO delivery rate (e.g. ppm, mg/kg IBW/hr, etc.), and/or the adverse event status of the NO delivery device. Exemplary input parameters from the LVAD include, but are not limited to, pump power, patient heart rate, blood flow through the pump, pulsatility index, LVAD pump speed, and/or the adverse event status of the LVAD. Exemplary output parameters from the control system to the NO delivery device include, but are not limited to, resetting/adjusting the NO delivery rate. Exemplary output parameters from the control system to the LVAD include, but are not limited to, resetting/adjusting the LVAD pump speed. Other relevant input/output parameters may also be used.

As set forth above, a control system coordinating operation of the LVAD and the NO delivery device may be used in any of the indications or methods described herein. In various embodiments of this aspect, the system comprises a control system in communication with the NO delivery device and/or the LVAD, wherein the control system monitors one or more parameters of the NO delivery device and/or one or more parameters of the LVAD. If one or more parameters of the NO delivery device and/or LVAD and/or of the patient are outside of a predetermined range, the control system may adjust the LVAD pump settings, the inhaled NO dose, initiate a weaning protocol and/or provide an alert. The system may also comprise the NO delivery device and/or the LVAD itself.

In one or more embodiments, the control system reduces a pump speed of the LVAD if there is a failure of the NO delivery device that discontinues NO administration. Failure of the NO delivery device can either be relatively minor or may be major. The control system may also initiate a weaning procedure for the NO delivery device if there is a failure of the LVAD and/or if the NO delivery device is going to be shutoff or if there is a failure of the NO delivery device. The control system may also adjust the inhaled NO dose and/or provide an alert if any of the monitored parameters are outside of the relevant range and/or if there is a failure of the LVAD and/or NO delivery device.

The control system may provide for autonomous control of LVAD and/or NO delivery device functionality once the control systems' "rules set" has been input by the clinician and once the devices have been initiated by the clinician. The rules set may consist of initial LVAD and NO system settings, input vs. output parameter relationships, alarm settings, communications configuration etc. It is understood that the rules set can be entered interactively (e.g. pump speed can be adjusted during patient assessment) or the rules set can be entered preemptively prior to patient use of the device(s). The rules set can be accessible through a menu-driven software program which allows the clinician to input all aspects of required system performance. Some of the rules the clinician enters may be statically set, i.e. the setting does not change once set. In some embodiments, a high pump speed alarm is an example of a static rule. The rules may define a variable input vs. output relationship over time; for instance, the pump speed might be commanded to be reduced over time or further the rules set may allow the controller to control parameter variation within predefined limits or control parameter variation through linear or non-linear control techniques in the which input/output parameter relationship can be controlled dynamically.

Menu-Driven Modes of Control

Figure 6:
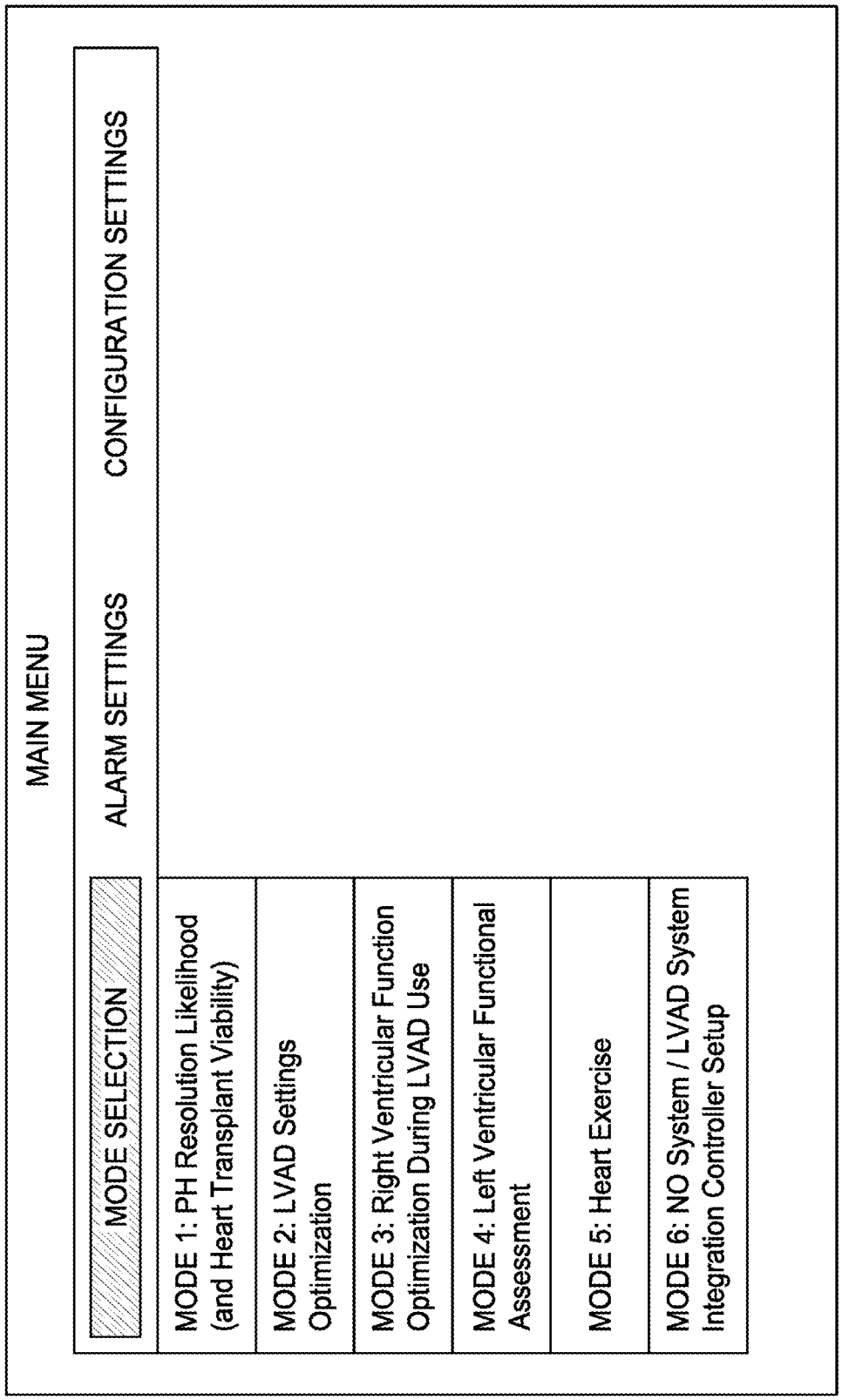
FIG. 6 illustrates an exemplary main menu with mode selection that can be used in accordance with one or more embodiments of the invention.
Figure 7:
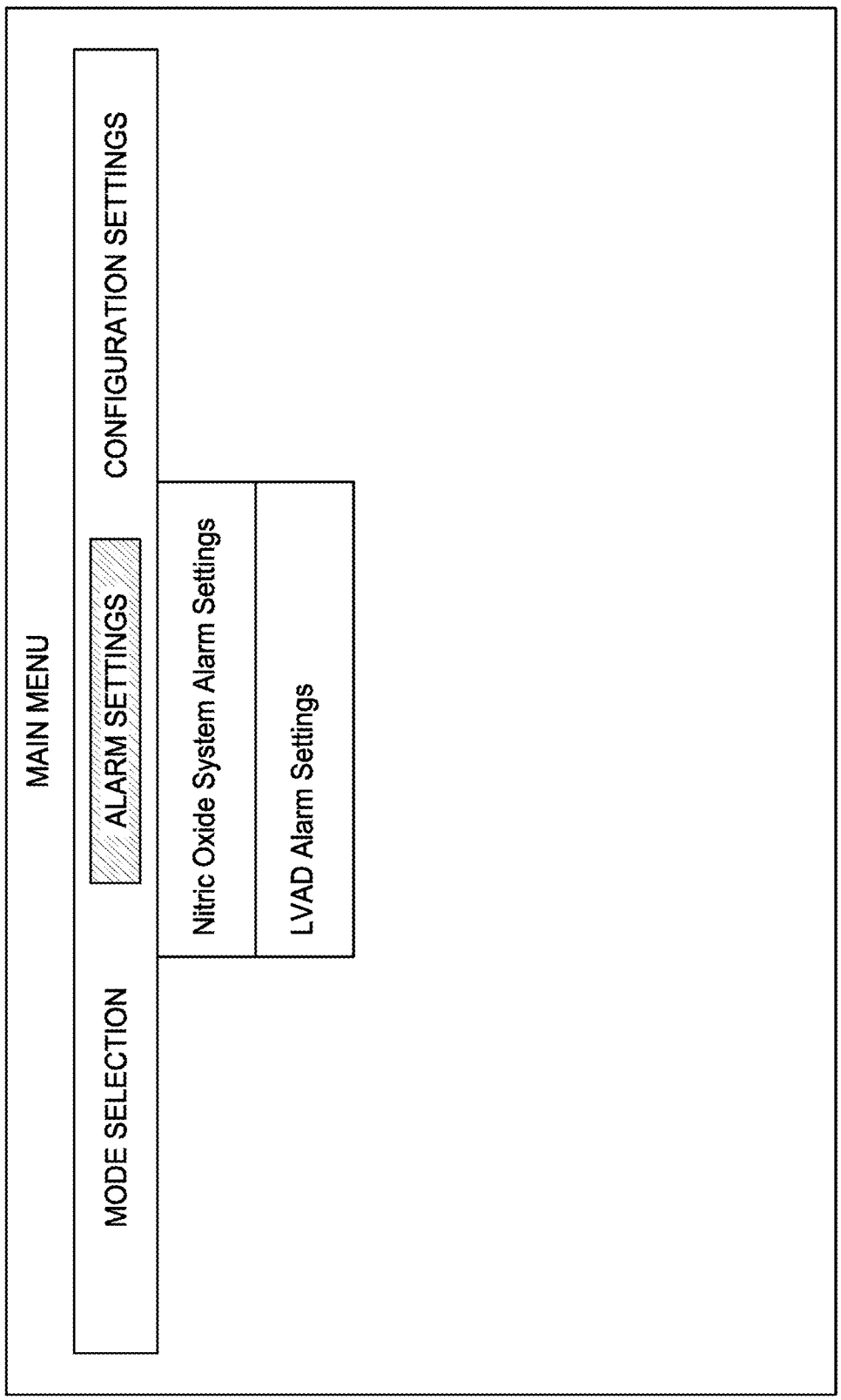
FIG. 7 illustrates an exemplary main menu with alarm settings that can be used in accordance with one or more embodiments of the invention.
Figure 8:
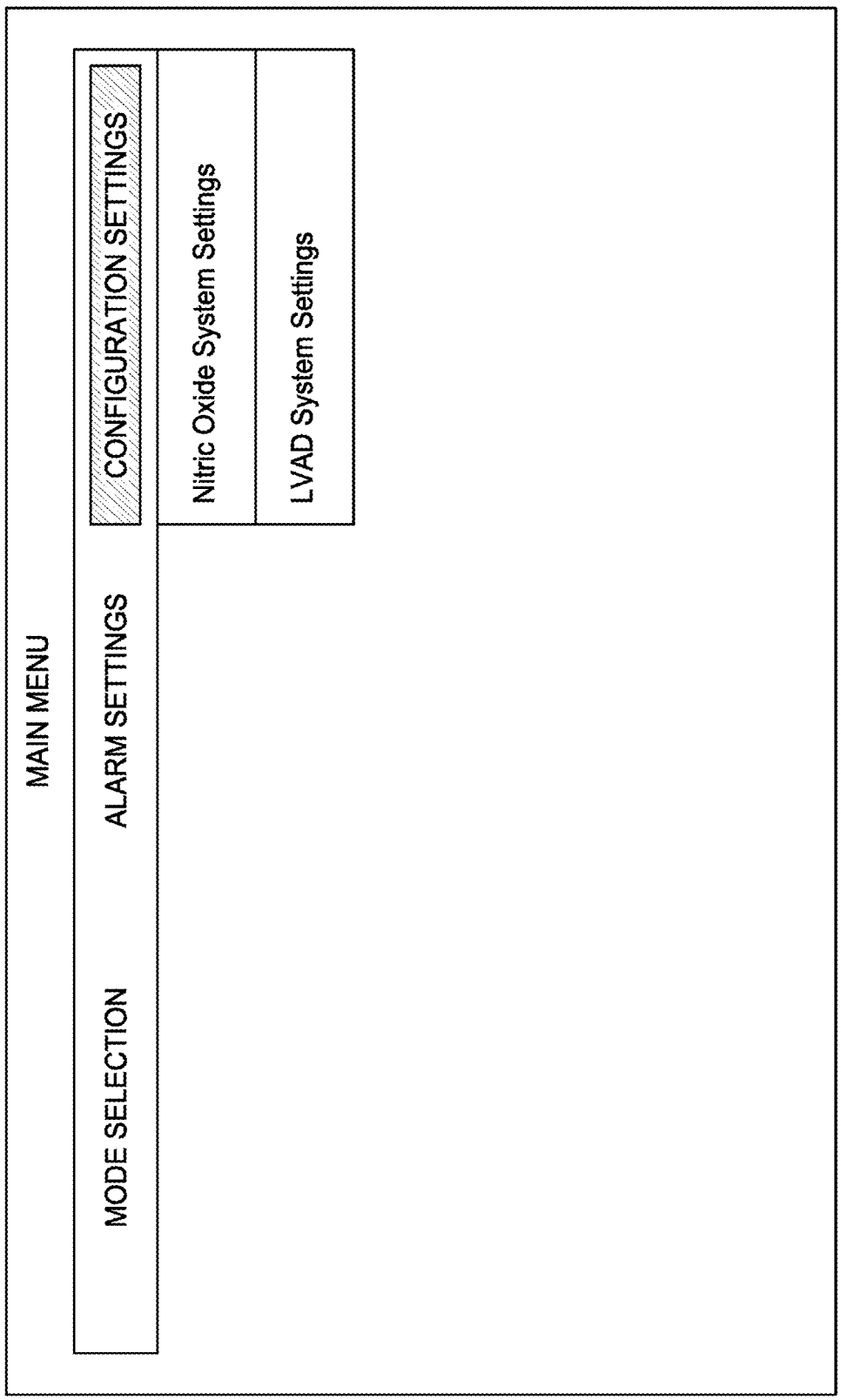
FIG. 8 illustrates an exemplary main menu with configuration settings that can be used in accordance with one or more embodiments of the invention.

In one or more embodiments, the control system user interface allows for selecting a number of menu-driven control schemes in which the operation of the NO delivery device and/or LVAD is controlled consistent with the clinical needs of the patient or clinician. An example of such a main user interface menu is shown in FIGS. 6-8. For example, FIG. 6 shows a menu that allows for the user to select a "mode" or control scheme, which can be any of the indications or methods described above. In some embodiments, when one particular mode is enabled, the other modes are disabled, i.e. the modes are user accessible with exclusivity. The menu can also include other user settable parameters such as alarm limits, NO delivery device and LVAD system configuration settings for therapy startup, weaning parameters, or for the case when an active mode is disabled (e.g. when a mode is disabled, the configuration settings would be used as default settings). FIG. 7 shows an exemplary alarm settings menu and FIG. 8 shows an exemplary menu for setting the NO delivery device and/or LVAD system configuration settings. These menus can include submenus for setting the alarms and/or configuration settings. In some embodiments, the alarms, NO delivery device settings and/or LVAD settings may have some options disabled based on the mode selection. Further, the settings in these configuration submenus can allow for default settings to be locked which are returned to when none of the mode selection options are active.

Exemplary modes are described in further detail below. These exemplary modes are not intended to be limiting, and fewer than all of these modes or additional modes can be provided in a menu-driven user interface of the control system.

Mode 1: PH Resolution Likelihood (and Heart Transplant Viability)

Figure 9:
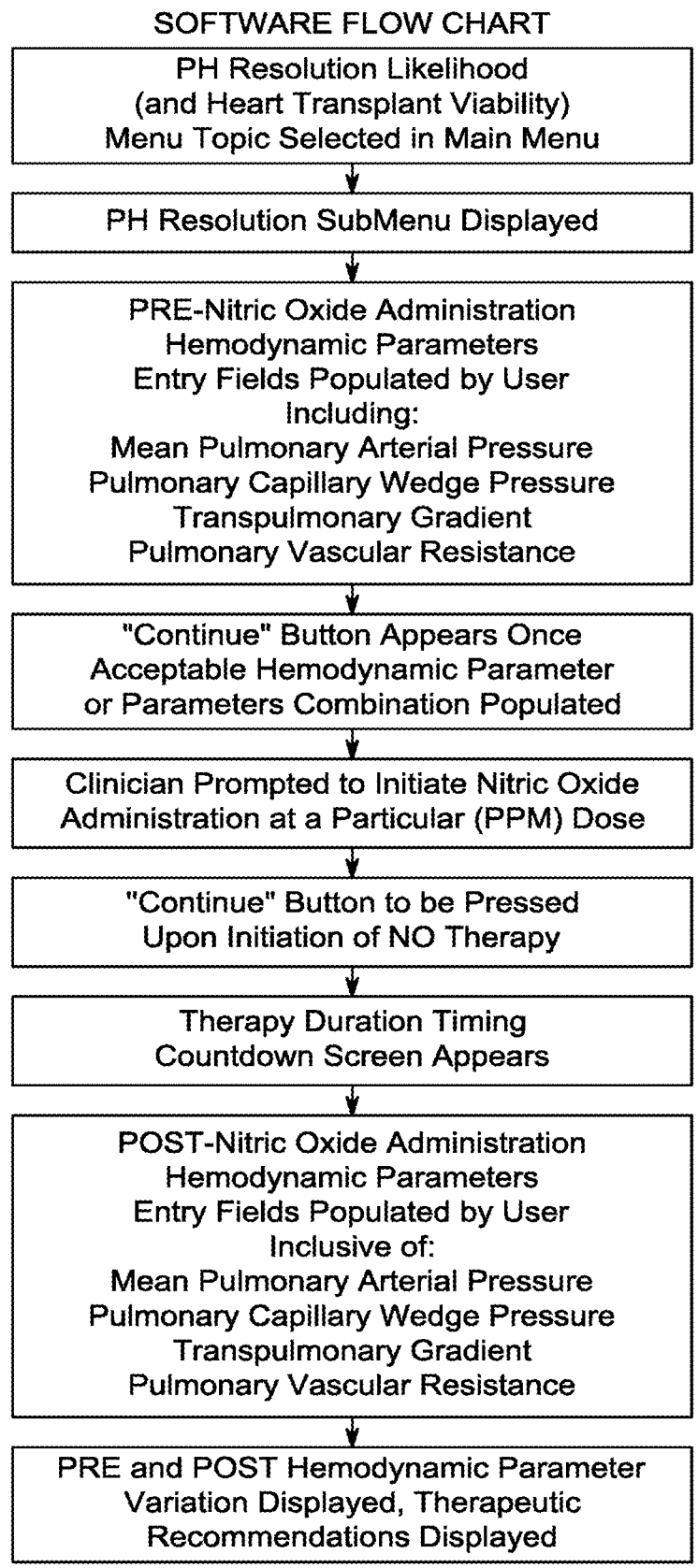
FIG. 9 illustrates an exemplary submenu for assessment of the likelihood of pulmonary hypertension resolution that can be used in accordance with one or more embodiments of the invention.

The Mode 1 submenu can include settings and operational flow aimed at determining the patient's hemodynamic response to inhaled NO administration for the purpose of determining if the patient might resolve pulmonary hypertension after continued use of the LVAD. In some embodiments, this mode can also be used to assess a patient's heart transplant viability. The mode can allow the user to input germane hemodynamic values before and/or after a NO delivery settings change. The results can be subject to clinical opinion or the results can be compared to acquired clinical study data and predictions for patient outcome provided by the software. FIG. 9 shows one embodiment of the program flow for the submenu relating to this mode.

Mode 2: LVAD Setting Optimization

Figure 10:
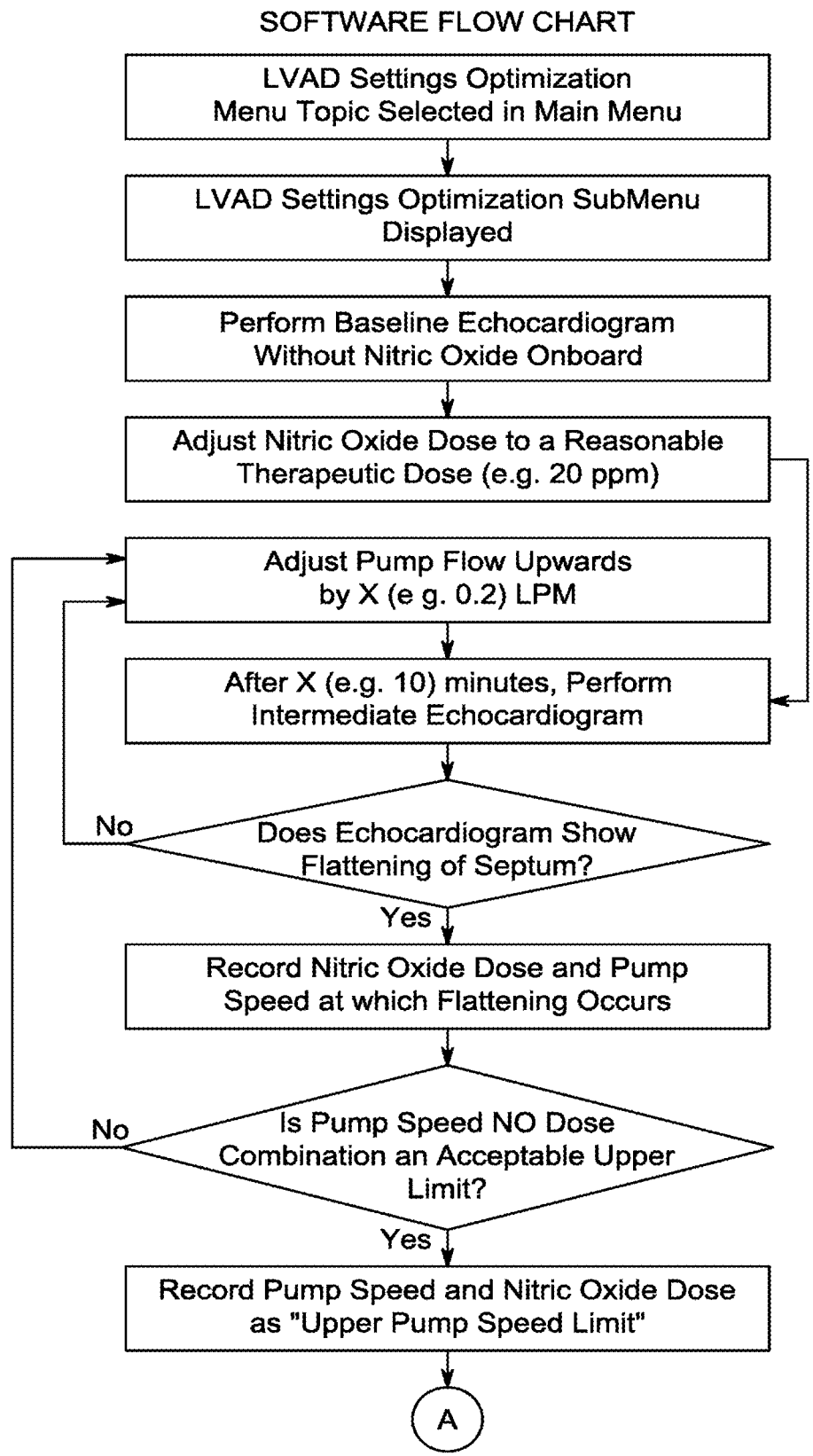
FIG. 10 illustrates an exemplary submenu for optimization of LVAD settings that can be used in accordance with one or more embodiments of the invention.
Figure 10:
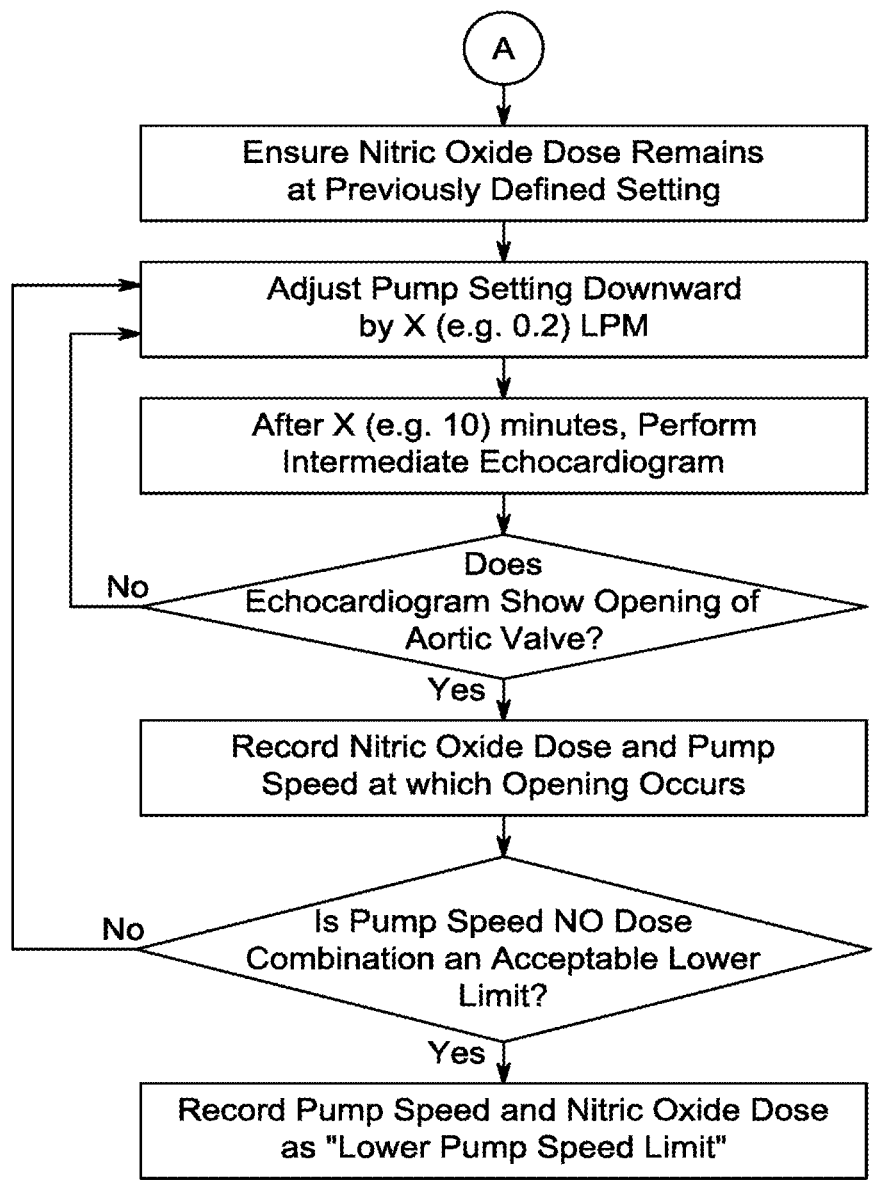

Mode 2 can include a method for determining the upper and lower limits of LVAD pump speed operation concurrent with inhaled NO delivery. FIG. 10 shows one embodiment of the program flow for the submenu relating to this mode. In this mode, the pump speed (or potentially other LVAD parameters) are adjusted during administration of NO in order that cardiac output can be optimized. Specifically, an echocardiogram is utilized in this mode to determine the low pump speed setting corresponding to the minimal pump speed necessary for the aortic valve to open with each heart beat and also to determine the high pump speed at which the septum of the heart flattens. In this mode, the user is prompted to make an initial nitric oxide setting and subsequent pump speed adjustments in the software. The software ultimately records the target pump speeds for utilization.

Mode 3: Right Ventricular Function Optimization During LVAD Use

Figure 11:
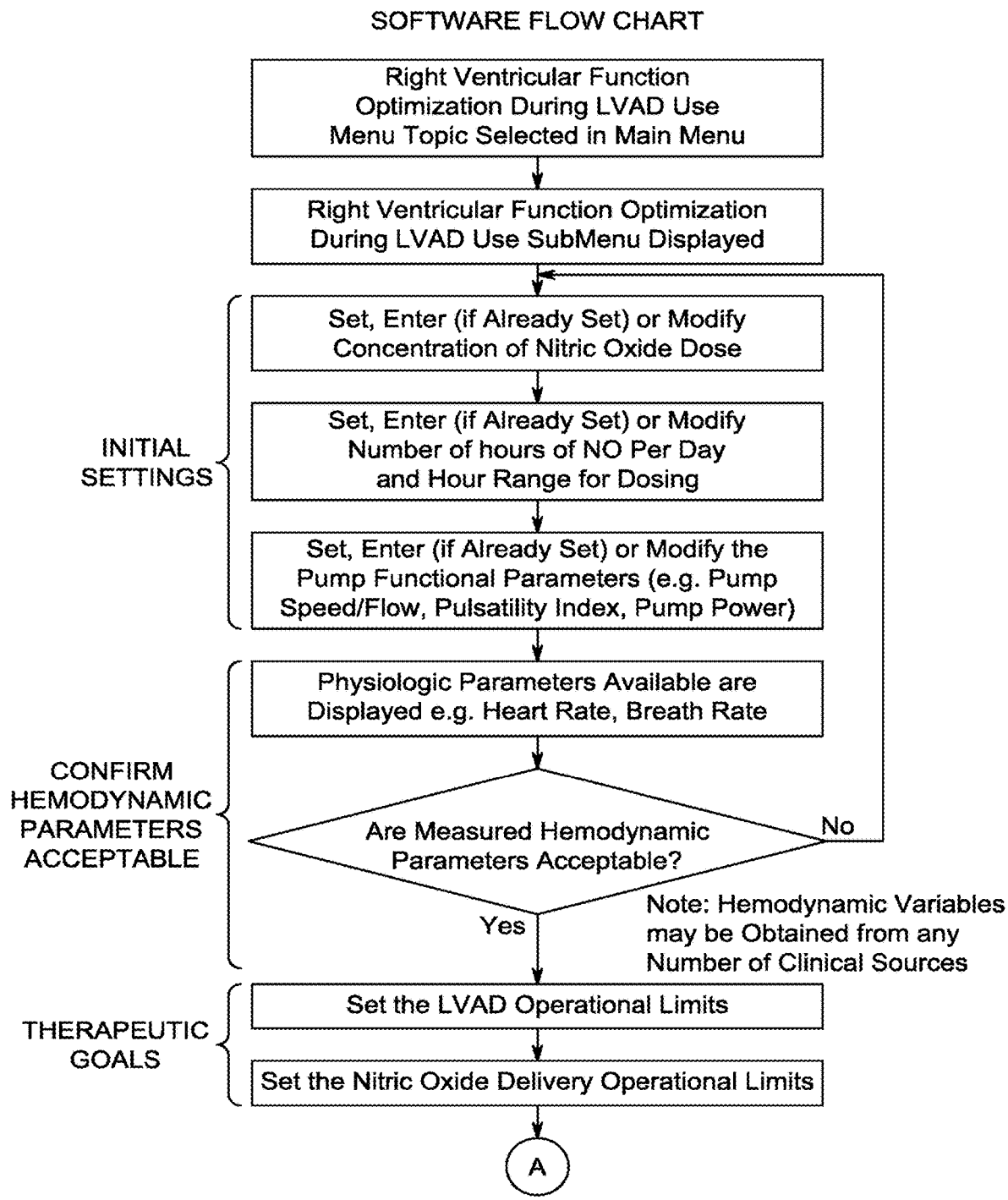
FIG. 11 illustrates an exemplary submenu for reducing the risk of right ventricular failure that can be used in accordance with one or more embodiments of the invention.
Figure 11:
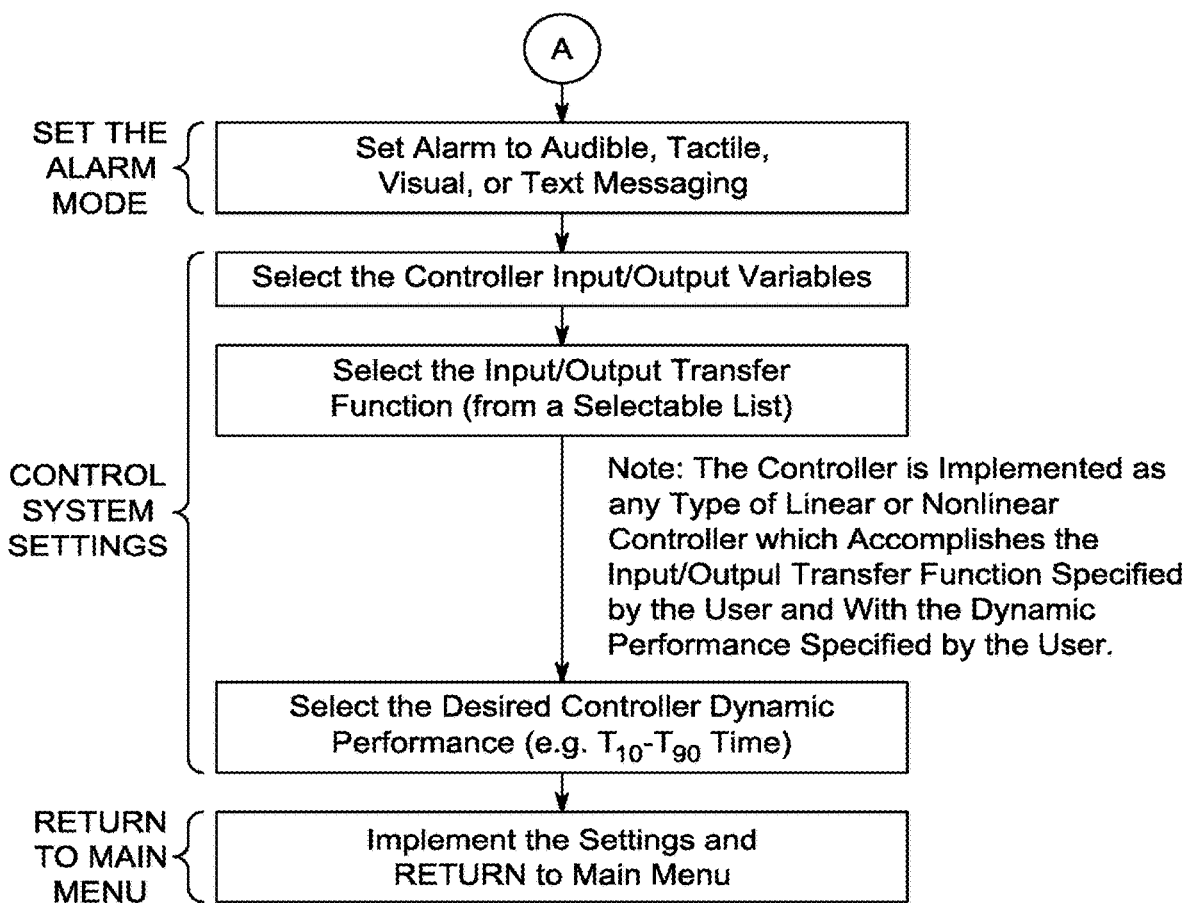

Mode 3 can provide a method for reducing the risk of right ventricular failure during LVAD use based on concurrent delivery of nitric oxide with LVAD use by making settings adjustments to both the NO dose and LVAD settings. FIG. 11 shows one embodiment of the program flow for the submenu relating to this mode. These settings can be adjusted manually (as shown in the first portion of the flow diagram in FIG. 11) or can be adjusted by a user defined control system and user defined transfer function and dynamic performance characteristics (see latter portion of flow diagram in FIG. 11). Monitoring of the patient can be performed by any number of clinical techniques including hemodynamic assessment. Finally, alarm limits for measured LVAD and NO delivery device parameters can be set.

Mode 4: Left Ventricular Functional Assessment

Figure 12:
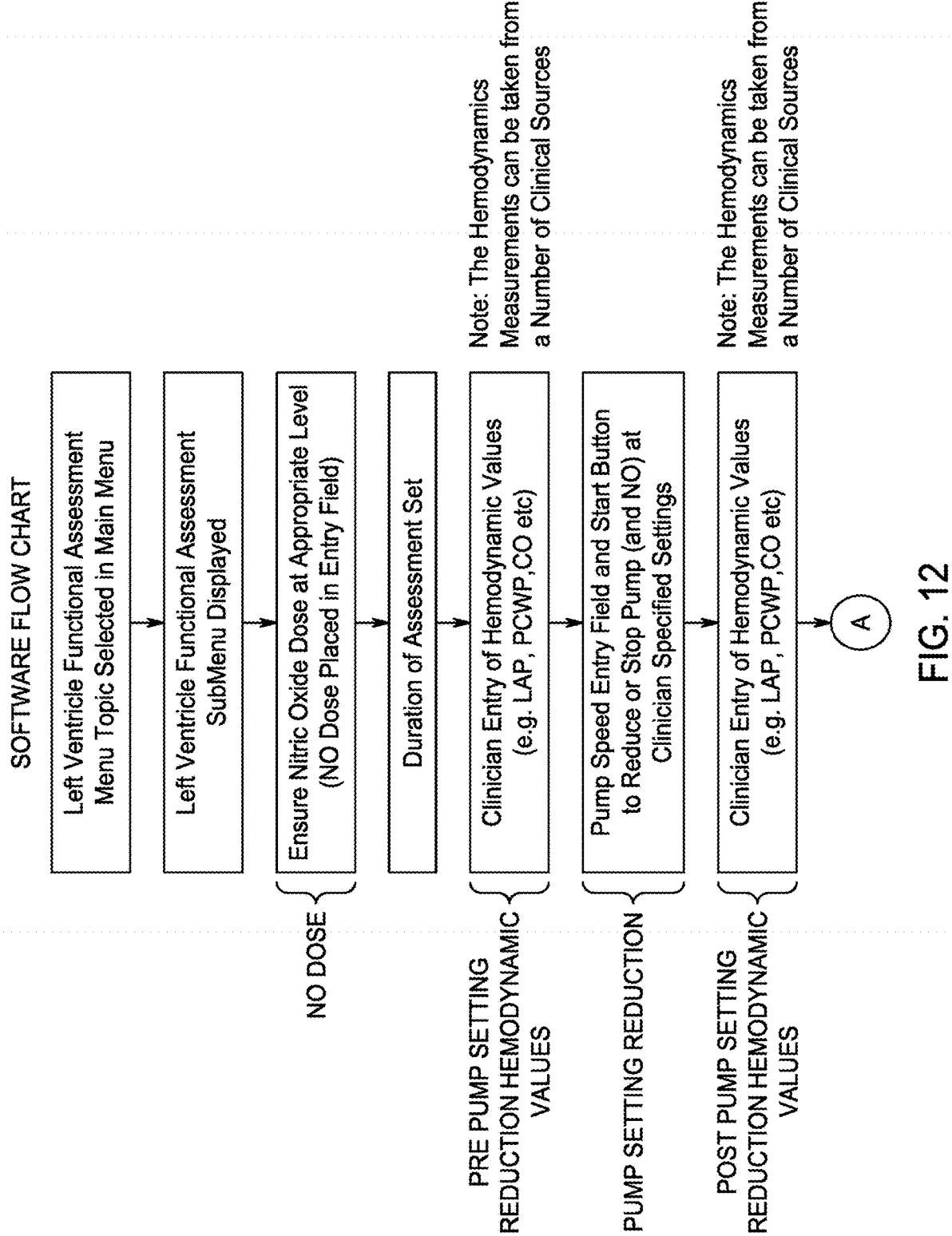
FIG. 12 illustrates an exemplary submenu for assessment of left ventricular function that can be used in accordance with one or more embodiments of the invention.
Figure 12:
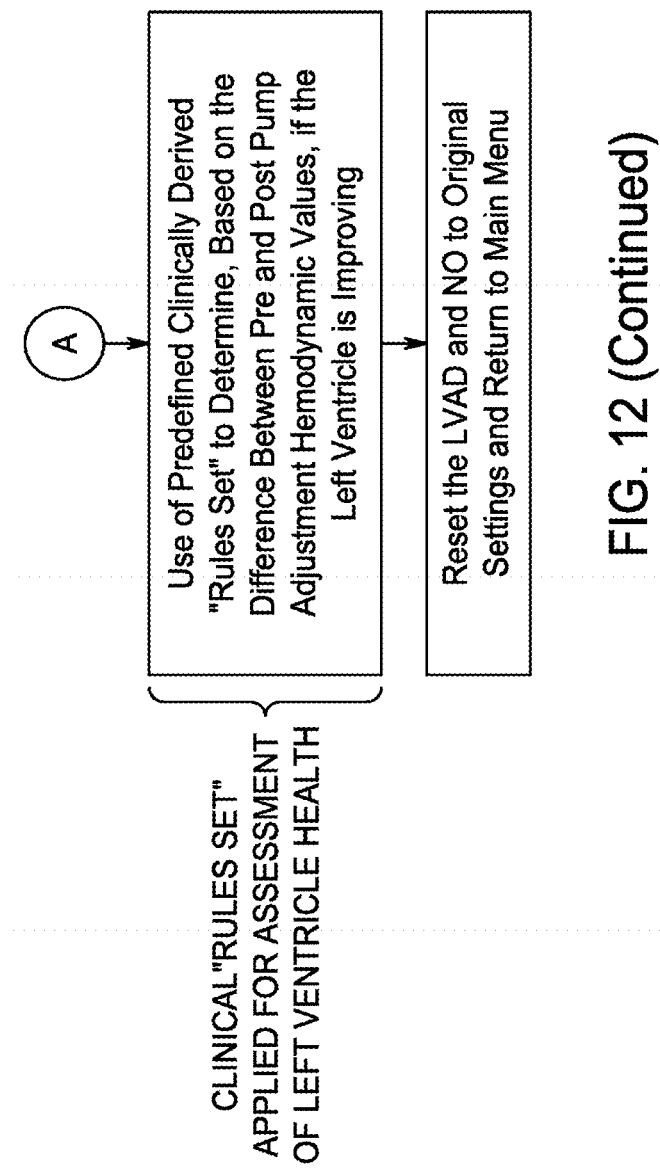

Mode 4 can be used to assess the status of left ventricular function following either a reduction in setting or complete cessation of the LVAD pump. FIG. 12 shows one embodiment of the program flow for the submenu relating to this mode. Ventricular function can be assessed by means of measured hemodynamic parameters such as LAP, PCWP or CO. Finally, pre- and post-pump speed adjustment hemodynamic parameter changes may be optionally assessed by a smart algorithm (see second to last box in FIG. 12) which provides clinical feedback based on these hemodynamic changes about the status of the left ventricle.

Mode 5: Heart Exercise Facility

Figure 13:
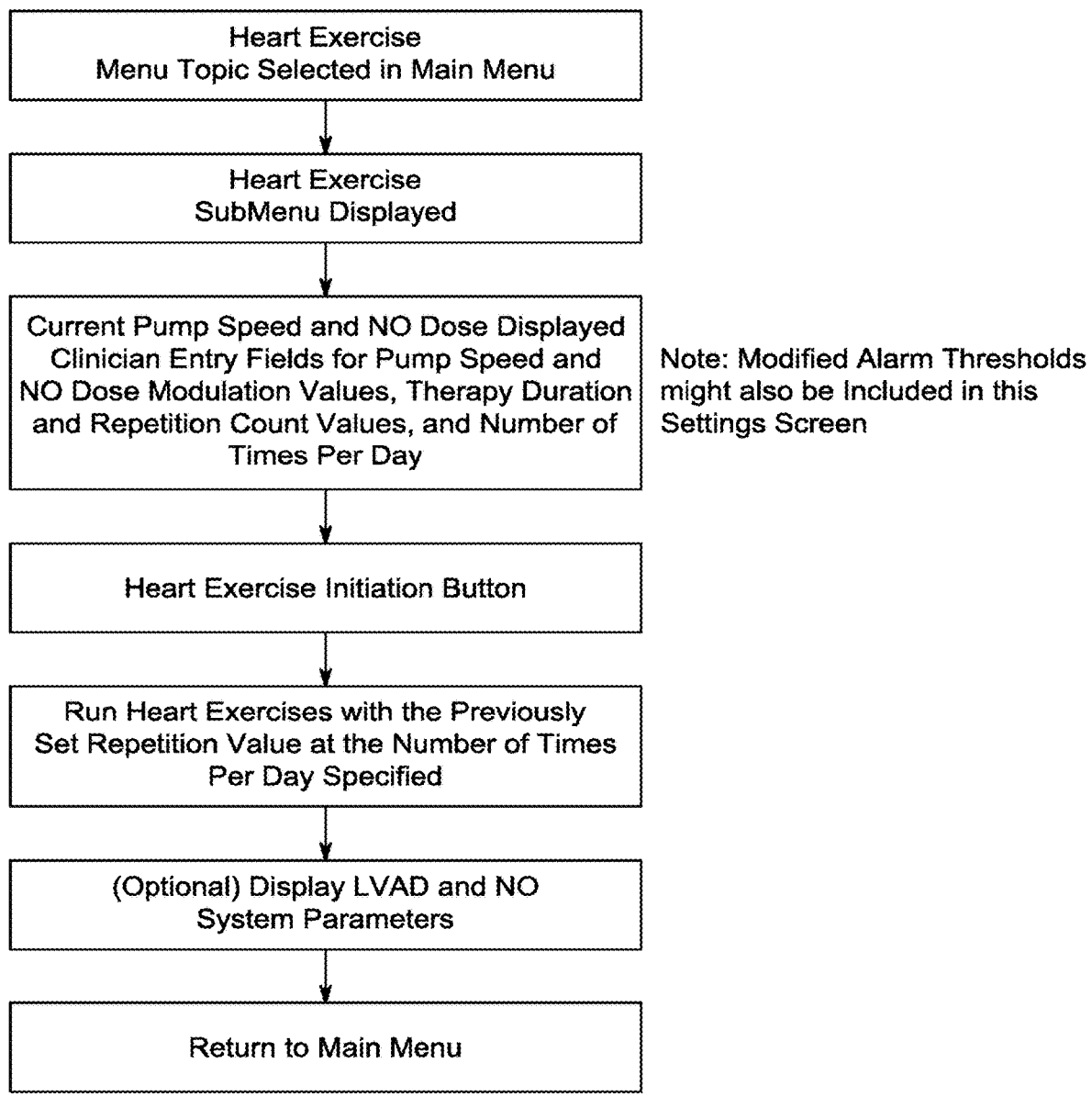
FIG. 13 illustrates an exemplary submenu for heart exercise that can be used in accordance with one or more embodiments of the invention.
Figure 14:
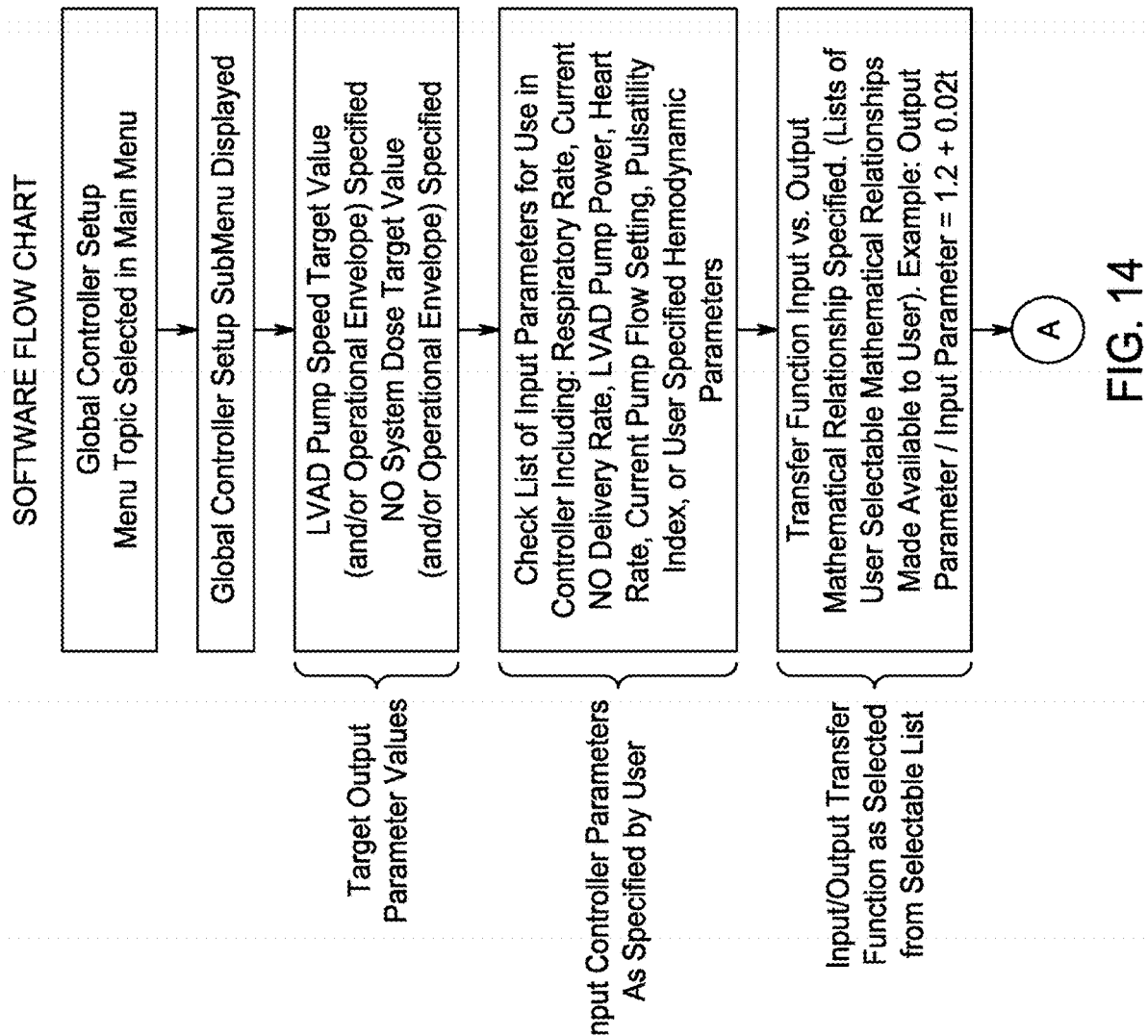
FIG. 14 illustrates an exemplary submenu for clinician setting of the control system that can be used in accordance with one or more embodiments of the invention.
Figure 14:
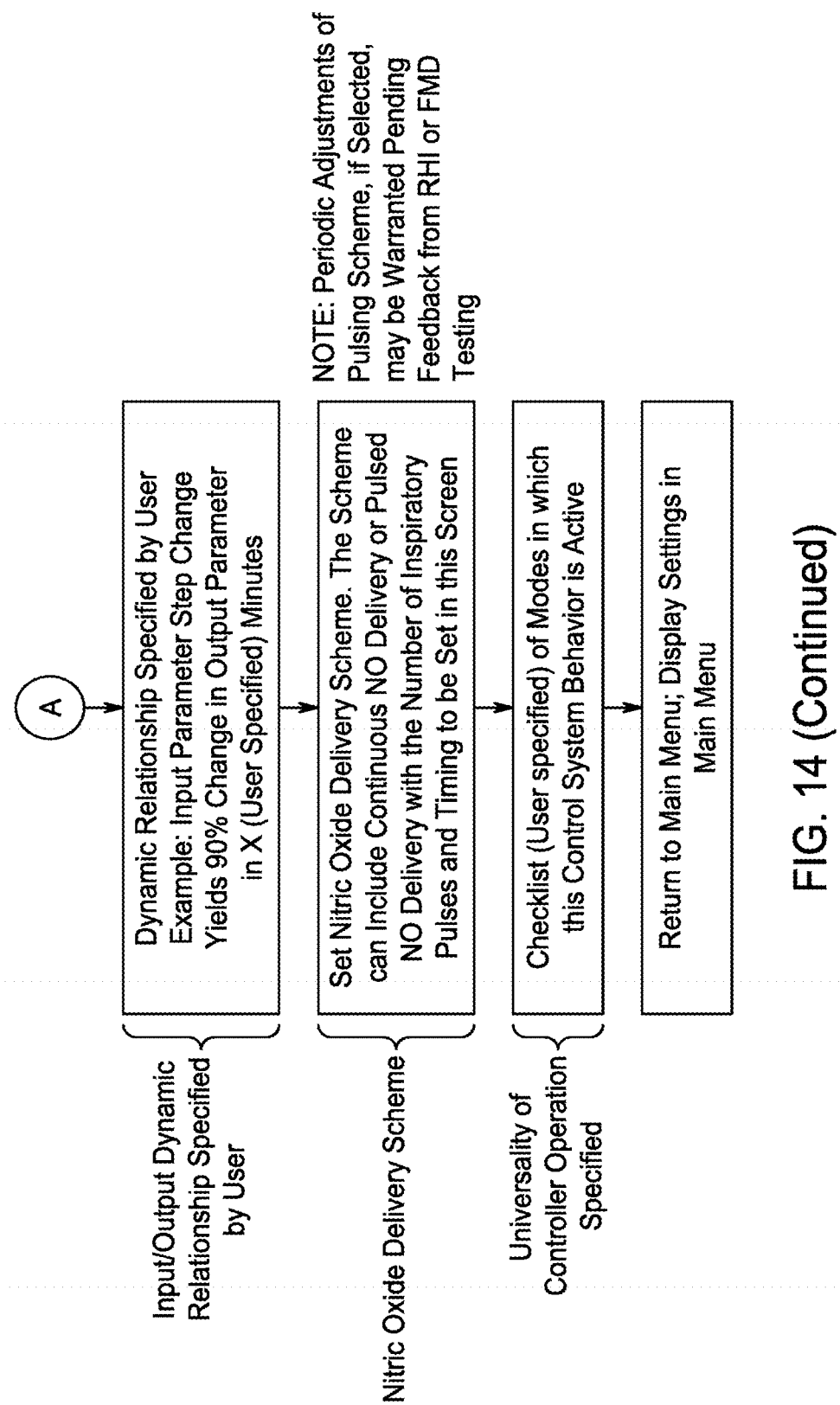

Mode 5 can be used to exercise the heart by first reducing the speed of or stopping the LVAD pump, then preloading the left ventricle by short term administration of NO and then subsequently cycling off and on the dose of NO to exercise the (left ventricle) heart. An exemplary submenu for implementing this mode is shown in FIG. 13.

Mode 6: Global Control System Settings

Mode 6 can be used to set the control system, which can oversee the functionality of the NO delivery device and/or the LVAD. This control system setting can be set to be the master control system used at all times during the operation of the invention or alternately it may be disabled in particular modes previously described. The control system settings can provide methods for adjustment of nitric oxide dose or LVAD pump speed based on the input parameters specified in FIG. 5 or alternately based on measured hemodynamic parameters input at timely intervals by the clinician. In this mode, the clinician can be allowed to specify the input parameters and also the transfer functions between single or multiple input parameters and the output parameters (e.g. pump speed and NO dose). The dynamic performance of this relationship can also be user specified. Finally, timed, respiratory cycle synchronized pulsed delivery of NO can also be specified. This may include single or multiple pulses of NO of fixed or time-varying concentration profiles. The ability of the clinician to turn on the controller (enabling output parameter variation in time) or to disable the controller in favor of making static (output) settings adjustments can also be specified. These settings can be displayed along with measured parameters and alarm settings (as specified in another main menu item) in the main menu screen in order that rapid assessment of patient status can be obtained by the clinician at a glance.

LVAD

The LVAD may be any appropriate LVAD prescribed by a physician, including, but not limited to, pulsatile, semi-pulsatile (such as those that perform pulsatile pump speed modulation), or continuous-flow LVADs. The LVAD can have any appropriate mechanism of providing blood flow, including, but not limited to, valves, centrifugal pumps, turbines, etc. The LVAD can be internal or external to the patient. In some embodiments, the LVAD is an internal LVAD that is implanted in the patient.

No Delivery Device

Figure 2:
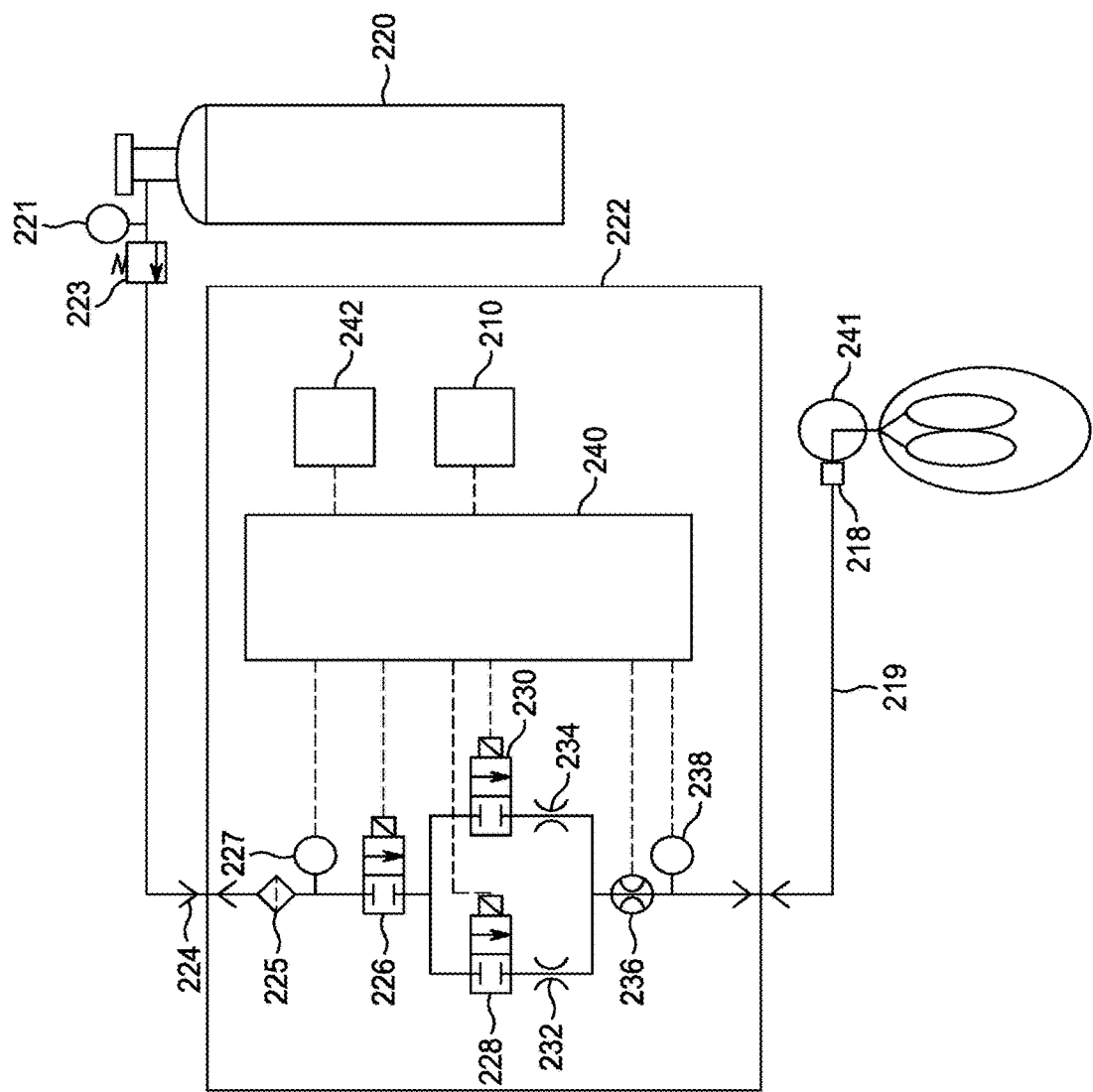
FIG. 2 illustrates an exemplary NO delivery device that can be used in accordance with one or more embodiments of the invention.

The NO delivery device may include any appropriate components for administering inhaled NO to the patient, including flow sensors, valves, flow controllers, processors, safety shut-off valves, purge valves, tubing etc. The NO delivery device may administer a constant concentration of inhaled NO, such as described by U.S. Pat. No. 5,558,083, which is hereby incorporated by reference in its entirety. An example of such a NO delivery device is shown in FIG. 1. The NO delivery device may administer a plurality of pulses of inhaled NO to provide a dose of inhaled NO that is independent of a patient's breathing pattern, such as described by U.S. Pat. No. 7,523,752, which is hereby incorporated by reference in its entirety. An example of such a NO delivery device is shown in FIG. 2. The NO delivery device may also have the features described in any of the following U.S. Patents and published U.S. Patent Applications, which are incorporated by reference in their entireties: U.S. Pat. Nos. 8,573,209; 8,573,210; 8,770,199; and U.S. Patent App. Pub. No. 2014/0283828. Other appropriate NO delivery devices are known in the art, such as the INOmax DSIR®, INOmax® DS and/or INOvent®.

In the exemplary NO delivery device shown in FIG. 1, a therapeutic injector module 103 is in fluid communication with a first inlet 101 and a second inlet 102. First inlet 101 is in fluid communication with therapeutic gas injector tube 110, which is in fluid communication with a therapeutic gas supply comprising NO. Second inlet 102 is in fluid communication with breathing gas delivery system 111, which is illustrated as a ventilator. The arrows in FIG. 1 indicate the direction of flow for the breathing gas and the combined gas mixture of therapeutic gas and breathing gas. Flow sensor 106 is in fluid communication and downstream of second inlet 102, and monitors the flow of breathing gas through therapeutic injector module 103. The top view of therapeutic injector module 103 is shown. The therapeutic gas and breathing gas mix in therapeutic injector module 103 to provide a gas mixture. Injector module cable 105 connects therapeutic injector module 103 with control module 109. Control module 109 comprises display 108, which can display information about NO delivery and/or any of the parameters described herein, and can provide any alerts as described herein. Inspiratory breathing hose 112 is in fluid communication with outlet 104 and nasal cannula 114 or other patient interface. The inspiratory breathing hose provides the gas mixture of breathing gas and therapeutic gas to nasal cannula 114, which delivers the gas mixture to the patient. Patient gas sample line 113 diverts some of the flow of the gas mixture from inspiratory breathing hose 112 and brings it to sample block 119 for measuring NO, $O_2$ and/or $NO_2$ concentrations in the gas delivered to the patient.

In the exemplary NO delivery device shown in FIG. 2, a supply tank 220 can be in fluid communication with a tank pressure gauge 221 and a regulator 223 to bring the tank pressure down to the working pressure of gas delivery device 222. The pharmaceutical gas can enter gas delivery device 222 through an inlet 224 that can provide a ready connection between delivery device 222 and supply tank 220 via a conduit. Gas delivery device 222 can have a filter 225 to ensure no contaminants can interfere with the safe operation of the device and/or a pressure sensor 227 to detect if the supply pressure is adequate and can thereafter include a gas shut off valve 226 as a control of the pharmaceutical gas entering deliver device 222 and to provide safety control in the event delivery device 222 is over delivering the pharmaceutical gas to the patient. In the event of such over delivery, shut off valve 226 can be immediately closed and an alarm 242 can be sounded to alert the user that the gas delivery device has been disabled. As such, shut off valve 226 can be a solenoid operated valve that can be operated from signals directed from a central processing unit including a microprocessor.

Downstream from shut off valve 226 can be a flow control system that controls the flow of the pharmaceutical gas to the patient through the gas conduit 219 to the patient device 218 to the patient 241. In exemplary embodiments, the flow control system can comprise a first flow control valve that can be a high flow control valve 228 and a second flow control valve that can be a low control valve 230 and there can be a first flow orifice that can be a high flow orifice 232 and a second flow orifice that can be a low flow orifice 234. The purpose and use of the flow valves 228, 230 and flow orifices 232, 234 will be later explained. A gas flow sensor 236 can also be located in the flow of pharmaceutical gas to patient device 218 and, as shown, can be downstream from the flow control system, however, gas flow sensor 236 may alternatively be located upstream of the flow control system.

Next, there can be a patient trigger sensor 238. When the patient breathes in during inspiration it can create a small sub atmospheric pressure in the nose or other area where patient device 218 is located, and hence in patient device 218 itself. Patient trigger sensor 238 can detect this pressure drop and can provide a signal indicative of the start of inspiration of the patient. Similarly, when the patient breathes out there can be a positive pressure in patient device 218 and patient trigger sensor 238 can detect that positive pressure and can provide a signal indicative of the beginning of expiration. This can allow patient trigger sensor 238 to determine not only the respiratory rate of the patient but also the inspiratory times and/or expiratory times. It will be understood that other techniques can be used to determine the respiratory rate of the patient, inspiratory times, and expiratory times, and/or other aspects of patient breathing.

There can also be a central processing unit (CPU) 240 that can communicate with patient trigger sensor 238, flow valves 228, 230, gas shut off valve 226, and other components in order to carry out various exemplary embodiments of the present disclosure. CPU 240 can include a processing component such as a microprocessor to carry out all of the solutions to the equations that can be used by the gas delivery device 222 to deliver the predetermined quantity of the pharmaceutical gas to a patient. The CPU 420 can he connected to the front panel 210 where the user can enter settings and monitor therapy.

Figure 3:
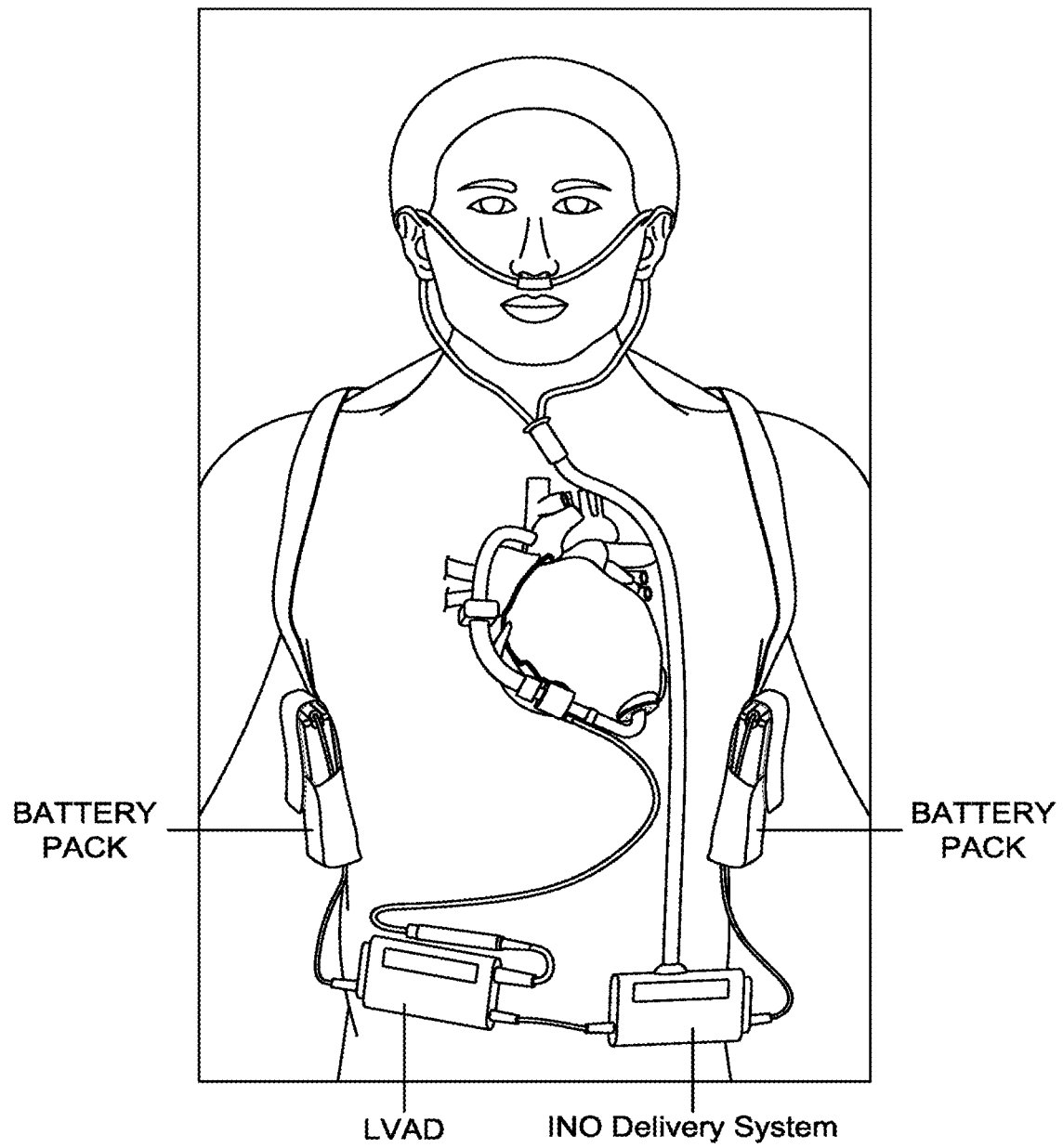
FIG. 3 illustrates an exemplary NO delivery device in communication with an LVAD that can be used in accordance with one or more embodiments of the invention.

As shown in FIG. 3, the NO delivery device may be in communication with the LVAD. In the embodiment shown in FIG. 3, the control system is integral to the NO delivery device. However, as described above, the control system can also be integral to the LVAD or can be a separate, stand-alone control module.

The NO delivery device may also include components for monitoring the gas that is administered to the patient, such as gas concentration sensors (e.g. $O_2$, NO and/or $NO_2$ sensors), sampling pumps, etc. The NO delivery device may also include redundant sensors and/or valves and have an automatic backup delivery system in case of failure of the primary NO delivery system. The NO delivery device may also include one or more sensors for feedback control of the NO delivery and/or for independent safety monitoring of NO delivery. The NO delivery device can also provide alarms if any of the monitored parameters meet or exceed a certain level or if other safety issues are present.

The NO delivery device may be portable and light (e.g., less than 10 lbs) so that it does not hinder the patient's mobility. The NO delivery device may run on a battery and have a battery life that meets a certain minimum criteria, such as having a battery life of at least 16 hours. The NO delivery device may also include a backup battery or other power source.

The NO source may include two or more gas cylinders such that continuous NO administration is not interrupted when one of the gas cylinders is replaced. Also, instead of a cylinder of NO-containing gas, the NO may be generated bedside, such as by an appropriate chemical reaction, e.g. the reaction of a NO-releasing agent and a reductant such as ascorbic acid. Other methods for generating nitric oxide bedside are also known in the art.

The NO delivery device may also include an automated pre-use checkout procedure with automatic purge to clear $NO_2$, and on-screen setup instructions. The system may also have on-screen alarm help, and wireless connectivity to communicate with an electronic medical record (EMR) system or a tech support desk for remote troubleshooting. Another safety feature may be the incorporation of sensors and mechanisms to automatically detect fluid or gas leaks.

The NO delivery device may have additional safety features such as a weaning protocol that slowly reduced the inhaled NO dose to avoid a sudden increase in PAP. Such a weaning protocol may be initiated by a "wean button" on the NO delivery device, or may initiated automatically by the control system in communication with the LVAD and/or the NO delivery device. The weaning protocol may include small changes in the NO dose, such as reducing the dose by 5 ppm for several minutes, followed by reducing the dose by a further 5 ppm for several minutes, until the patient is completely weaned off of the inhaled NO. Other increments for a weaning protocol include 0.1 ppm, 0.2 ppm, 0.5 ppm, 1 ppm, 2 ppm, 3 ppm, 4 ppm, 5 ppm, 6 ppm, 7 ppm, 8 ppm, 9 ppm, 10 ppm, 15 ppm and 20 ppm, or 0.1, 0.2, 0.5, 1, 2, 3, 4, 5, 6, 7, 8, 9, 10, 15, 20, 25, 30, 35, 40 or 50 µg/kg IBW/hr. Multiple weaning protocols may be used based on the failure detected and whether device shutoff is eminent. The weaning protocol may also be individualized for a particular patient, such as having the weaning protocol be dependent on the degree of the patient's current and/or prior PH.

As described above, in some embodiments the inhaled NO dose is adjusted in response to the monitoring of various parameters of the LVAD and/or the patient. Such adjustments can include an increase or a decrease in the inhaled NO dose (either in ppm or µg/kg IBW/hr). Increments for an adjustment include 0.1 ppm, 0.2 ppm, 0.5 ppm, 1 ppm, 2 ppm, 3 ppm, 4 ppm, 5 ppm, 6 ppm, 7 ppm, 8 ppm, 9 ppm, 10 ppm, 15 ppm and 20 ppm, or 0.1, 0.2, 0.5, 1, 2, 3, 4, 5, 6, 7, 8, 9, 10, 15, 20, 25, 30, 35, 40 or 50 µg/kg TBW/hr.

In accordance with the invention, a method of determining whether a patient with pulmonary hypertension will resolve the pulmonary hypertension with continued use of a left ventricular assist device (LVAD) is provided. The method may include measuring one or more pulmonary hemodynamic parameters of a patient with an LVAD to obtain a first pulmonary hemodynamic value; after obtaining the first pulmonary hemodynamic value, administering inhaled nitric oxide to the patient with the LVAD; and measuring one or more pulmonary hemodynamic parameters of the patient during or after the inhaled nitric oxide administration to obtain a second pulmonary hemodynamic value. The decrease in the pulmonary hemodynamic parameter from the first pulmonary hemodynamic value to the second pulmonary hemodynamic value of at least 10 mm Hg and/or at least 20% indicates that the patient is likely to resolve the pulmonary hypertension after continued use of the LVAD.

The method may further include selecting the pulmonary hemodynamic parameter from mean pulmonary artery pressure (mPAP), transpulmonary gradient (TPG) and pulmonary vascular resistance (PVR). The method may further include administering the nitric oxide at a concentration of 5 to 80 ppm for at least 10 minutes.

In accordance with the invention, the method may include measuring one or more pulmonary hemodynamic parameters by performing a right heart catheterization. The patient may be placed on a heart transplant list if the decrease in the pulmonary hemodynamic parameter from the first pulmonary hemodynamic value to the second pulmonary hemodynamic value is at least 10 mm Hg and/or at least 20%. The LVAD may be explanted and a donor heart is implanted in the patient.

In accordance with the invention, a method of optimizing the settings of a left ventricular assist device (LVAD) is provided. The method may include administering inhaled nitric oxide to a patient having an LVAD; performing an echocardiogram on the patient during the administration of inhaled nitric oxide; and adjusting or setting one or more parameters of the LVAD during the echocardiogram and during the administration of inhaled nitric oxide to optimize cardiac output. The adjusting or setting of one or more parameters of the LVAD may include one or more of (i) determining a low pump speed setting for the LVAD based on the minimal pump speed necessary for the patient's aortic valve to open with each heart beat or (ii) determining a high speed setting for the LVAD based on the pump speed at which the septum of the patient's heart flattens. The inhaled nitric oxide may be administered at a concentration of 5 to 80 ppm for at least 10 minutes.

In accordance with the invention, a method of reducing the risk of right ventricular failure during left ventricular assist device (LVAD) use is provided. The method may include administering inhaled nitric oxide to a patient with an LVAD for at least 12 hours a day for at least 20 days to reduce the risk of right ventricular failure, and confirming that the LVAD is functioning before administering inhaled nitric oxide. The inhaled nitric oxide may be administered after a patient has been weaned from cardiopulmonary bypass (CPB), and may be administered for at least 30 days, or at least 3 months. The inhaled nitric oxide may be administered at a concentration of 5 to 80 ppm or at a dose of 25 to 150 µg/kg IBW/hr.

The method may further include monitoring one or more output parameters of the LVAD and/or one or more hemodynamic parameters of the patient, comparing the one or more output parameters and/or the one or more hemodynamic parameters to a predetermined range, adjusting the dose of inhaled nitric oxide if the one or more outputs parameters and/or the one or more hemodynamic parameters are outside of the predetermined range, and providing an alert if the one or more output parameters and/or the one or more hemodynamic parameters are outside of the predetermined range.

In accordance with the invention, a method of monitoring the left ventricle of a patient with a left ventricular assist device (LVAD) is provided. The method may include reducing the pump speed of the LVAD or turning off the LVAD; measuring one or more pulmonary hemodynamic parameters of the patient to obtain a first pulmonary hemodynamic value; preloading the left ventricle by administering inhaled nitric oxide to the patient; and measuring one or more pulmonary hemodynamic parameters of the patient after or during administration of inhaled nitric oxide to obtain a second pulmonary hemodynamic value. The pulmonary hemodynamic parameter may be selected from left atrial pressure (LAP), pulmonary capillary wedge pressure (PCWP) and cardiac output (CO). The inhaled nitric oxide may be administered at a concentration of 5 to 80 ppm for at least 10 minutes. Treatment may be modified by explanting the LVAD from the patient if the left ventricle is improving. An increase in LAP and/or PCWP from the first pulmonary hemodynamic value to the second pulmonary hemodynamic value of less than 5 mm Hg may indicate that the left ventricle is improving.

In accordance with the invention, a method of exercising a heart of a patient having a left ventricular assist device (LVAD) is provided. The method may include reducing the pump speed of the LVAD or turning off the LVAD; preloading the left ventricle by administering inhaled nitric oxide to the patient for at least 5 minutes; discontinuing the inhaled nitric oxide administration; and repeating the preloading and discontinuation to exercise the left ventricle of the patient's heart. The preloading of the left ventricle may include administering inhaled nitric oxide at a concentration of 5 to 80 ppm for a time period in the range from 5 to 30 minutes, and may be performed one to five times a day.

In accordance with the invention, a method of reducing the risk adverse events during use of a continuous-flow or semi-pulsatile left ventricular assist device (LVAD) is provided. The method may include administering inhaled nitric oxide to a patient with a continuous-flow or semi-pulsatile LVAD for at least 12 hours a day for at least 20 days. The adverse events may be associated with reduced pulsatility and/or associated with impaired NO-mediated vascular function. Before administering inhaled nitric oxide, function of the LVAD may be confirmed. The inhaled nitric oxide may be administered after a patient has been weaned from cardiopulmonary bypass (CPB), and may be administered for at least 30 days or 30 months. The inhaled nitric oxide may be administered at a concentration of 5 to 80 ppm or at a dose of 25 to 150 µg/kg IBW/hr.

The method may further include monitoring one or more output parameters of the LVAD and/or one or more hemodynamic parameters of the patient, comparing the one or more output parameters and/or the one or more hemodynamic parameters to a predetermined range, and adjusting the dose of inhaled nitric oxide if the one or more outputs parameters and/or the one or more hemodynamic parameters are outside of the predetermined range. An alert may be provided if the one or more output parameters and/or the one or more hemodynamic parameters are outside of the predetermined range.

In accordance with the invention, a method of optimizing the dose of inhaled nitric oxide for use with a continuous-flow or semi-pulsatile left ventricular assist device (LVAD) is provided. The method may include measuring endothelial function of a patient having a continuous-flow or semi-pulsatile LVAD; administering inhaled nitric oxide to the patient at a first dose; measuring the endothelial function of the patient during the administration of inhaled nitric oxide; and adjusting the dose of inhaled nitric oxide to optimize endothelial function. The measuring the endothelial function of the patient comprises measuring one or more of (i) flow-mediated dilation (FMD) or (ii) reactive hyperemic index (RUT).

The method may include measuring one or NO-related molecules and/or other biomarkers of endothelial function in the patient's blood and/or plasma. The NO-related molecules may be selected from the group consisting of nitrite ($NO_2$), nitrate ($NO_3$) and nitrosohemoglobin.

In accordance with the invention, a system is provided. The system may include a control system in communication with a nitric oxide delivery device and/or a left ventricular assist device (LVAD), wherein the control system monitors one or more parameters of the nitric oxide delivery device and/or one or more parameters of the LVAD and provides an alert if one or more parameters of the nitric oxide delivery device and/or the LVAD are outside of a predetermined range. The control system may reduce a pump speed of the LVAD if there is a failure of the nitric oxide delivery device. The control system may initiate a weaning procedure for the nitric oxide delivery device if there is a failure of the LVAD. The control system may be integral to the nitric oxide delivery device, integral to the LVAD or a component of a stand-alone control module. The system may include the nitric oxide delivery device and the LVAD.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of monitoring the left ventricle of a patient with a left ventricular assist device (LVAD), the method comprising:

providing, via a display on a nitric oxide (NO) delivery device, clinician entry fields comprising pump speed, dose of inhaled NO, therapy duration, and number of times per day;

receiving input for each of the clinician entry fields;

reducing the pump speed of the LVAD to the received pump speed;

measuring one or more pulmonary hemodynamic parameters of the patient to obtain a first pulmonary hemodynamic value;

preloading the left ventricle by administering, via the NO delivery device, the received NO dose for the received therapy duration, wherein the NO dose is at a concentration of 5 to 80 ppm of NO and the therapy duration is for 5 to 30 minutes;

measuring one or more pulmonary hemodynamic parameters of the patient after or during administration of the dose of inhaled NO to obtain a second pulmonary hemodynamic value;

comparing the one or more hemodynamic parameters to a predetermined range;

adjusting the dose of inhaled NO if the one or more hemodynamic parameters are outside of the predetermined range; and displaying the pump speed and the NO dose currently being delivered;

providing an exercise initiation button and receiving input from the exercise initiation button; and exercising the heart, the exercising comprising:
discontinuing the inhaled NO administration; and
repeating the preloading, adjusting, and discontinuation to exercise the left ventricle of the patient's heart for the received number of times per day,
wherein the exercising steps are automated by the NO delivery device.

2. The method of claim 1, wherein the pulmonary hemodynamic parameter is selected from left atrial pressure (LAP), pulmonary capillary wedge pressure (PCWP) and cardiac output (CO).

3. The method of claim 1, wherein an increase in LAP and/or PCWP from the first pulmonary hemodynamic value to the second pulmonary hemodynamic value of less than 5 mm Hg indicates that the left ventricle is improving.

4. The method of claim 3, further comprising modifying treatment if the left ventricle is improving, the modifying comprising explanting the LVAD from the patient.

5. The method of claim 1, wherein measuring one or more pulmonary hemodynamic parameters comprises monitoring one or more output parameters of the LVAD.

* * * * *